(12) United States Patent
Breegi

(10) Patent No.: US 11,439,554 B2
(45) Date of Patent: *Sep. 13, 2022

(54) DISPOSABLE INFANT INCUBATOR AND DISPOSABLE CONTAINED MICROENVIRONMENT FOR STATIONARY OR TRANSPORT CASES

(71) Applicant: BREEGI SCIENTIFIC, INC., Brookline, MA (US)

(72) Inventor: Wisam Breegi, Woburn, MA (US)

(73) Assignee: BREEGI SCIENTIFIC, INC., Brookline, MA (US)

( * ) Notice: Subject to any disclaimer, the term of this patent is extended or adjusted under 35 U.S.C. 154(b) by 192 days.

This patent is subject to a terminal disclaimer.

(21) Appl. No.: 16/481,621

(22) PCT Filed: Feb. 2, 2018

(86) PCT No.: PCT/US2018/016581
§ 371 (c)(1),
(2) Date: Jul. 29, 2019

(87) PCT Pub. No.: WO2018/144809
PCT Pub. Date: Aug. 9, 2018

(65) Prior Publication Data
US 2019/0380901 A1 Dec. 19, 2019

Related U.S. Application Data

(60) Provisional application No. 62/454,283, filed on Feb. 3, 2017.

(51) Int. Cl.
*A61G 11/00* (2006.01)
*A61B 90/40* (2016.01)
*A61G 10/00* (2006.01)

(52) U.S. Cl.
CPC ............... *A61G 11/00* (2013.01); *A61B 90/40* (2016.02); *A61G 10/005* (2013.01)

(58) Field of Classification Search
CPC ........ A61G 11/00; A61G 11/009; A61G 10/00; A61G 10/005; A61G 10/02; A61G 10/04
See application file for complete search history.

(56) References Cited

U.S. PATENT DOCUMENTS

| 2,473,033 A | 6/1949 | Roger |
| 2,699,775 A | 1/1955 | Robert |

(Continued)

FOREIGN PATENT DOCUMENTS

| CN | 103796623 A | 2/2017 |
| JP | 2008191866 A | 8/2008 |

(Continued)

OTHER PUBLICATIONS

The International Preliminary Report on Patentability dated Nov. 24, 2015 for corresponding PCT Applicaiton No. PCT/US2014/038698.

*Primary Examiner* — John P Lacyk
(74) *Attorney, Agent, or Firm* — Nixon Peabody LLP; David S. Resnick; Susanna C. Benn

(57) ABSTRACT

A neonatal infant incubator apparatus (10) and a control system module (17), and methods and systems for using the control system module to control the microenvironment of the contained space (16) of the infant incubator apparatus (10). The neonatal infant incubator apparatus (10) including a collapsible frame (12) and a disposable housing (14) to create a closed contained space (16) with a controlled microenvironment. The control system module (17) is comprises a battery (32) and is configured to operate with low voltage; the control system module (17) configured to control the microenvironment, including regulating the temperature and gas composition, of the contained space (16), (Continued)

and includes an air circulation system (72) in air and/or fluid communication with the contained space (16). The systems, apparatus and methods are suitable for containing a full-term or premature infant in need of care in areas where power sources are limited, including e.g., rural or remote regions, third world countries, in a regular clinical setting and/or for transportation of the infant.

20 Claims, 12 Drawing Sheets

(56) References Cited

U.S. PATENT DOCUMENTS

| | | | |
|---|---|---|---|
| 2,915,074 A | 12/1959 | Robert | |
| 3,000,379 A | 9/1961 | Viers | |
| 3,710,791 A | 1/1973 | Deaton | |
| 3,818,896 A | 6/1974 | Deaton | |
| 3,850,172 A | 11/1974 | Cazalis | |
| 4,000,749 A | 1/1977 | Busco | |
| 4,077,417 A | 3/1978 | Beavers | |
| 4,275,719 A | 6/1981 | Mayer | |
| 4,367,728 A | 1/1983 | Mutke | |
| 4,407,280 A | 10/1983 | Trammell et al. | |
| 4,550,713 A | 11/1985 | Hyman | |
| 4,612,916 A | 9/1986 | Akers et al. | |
| 4,950,222 A | 8/1990 | Scott et al. | |
| 4,939,803 A | 10/1990 | Waters | |
| 5,061,235 A | 10/1991 | Hogan | |
| 5,113,854 A | 5/1992 | Dosch et al. | |
| 5,316,541 A | 5/1994 | Fischer | |
| 5,333,634 A | 8/1994 | Taylor | |
| 5,342,121 A | 8/1994 | Koria | |
| 5,495,857 A | 3/1996 | Fegan | |
| 5,728,041 A | 3/1998 | Fowler | |
| 6,001,057 A | 12/1999 | Bongiovanni et al. | |
| 6,217,099 B1 | 4/2001 | McKinney et al. | |
| 6,321,764 B1 | 11/2001 | Gauger et al. | |
| 6,354,316 B1 | 3/2002 | Chen | |
| 6,367,476 B1 * | 4/2002 | Conn | A61G 10/04 128/205.26 |
| 6,418,932 B2 | 7/2002 | Paschal et al. | |
| 6,461,290 B1 | 10/2002 | Reichman et al. | |
| 6,500,111 B1 | 12/2002 | Salmon et al. | |
| 6,508,850 B1 | 1/2003 | Kotliar | |
| 7,406,978 B2 | 8/2008 | Mintie et al. | |
| 7,481,234 B1 | 1/2009 | Gustason et al. | |
| 7,503,890 B2 | 3/2009 | Kubicsko et al. | |
| 7,818,835 B2 | 10/2010 | Heaton et al. | |
| 8,245,713 B2 | 8/2012 | Paschal et al. | |
| 2001/0029955 A1 | 10/2001 | Paschal et al. | |
| 2002/0045796 A1 * | 4/2002 | O'Connor | A61B 90/40 600/21 |
| 2002/0147381 A1 | 10/2002 | Kolarovic | |
| 2004/0133064 A1 | 7/2004 | Castillon Levano et al. | |
| 2005/0097829 A1 | 5/2005 | Seo | |
| 2006/0247487 A1 | 11/2006 | Arts et al. | |
| 2007/0056593 A1 | 3/2007 | Kubicsko et al. | |
| 2007/0151588 A1 | 7/2007 | Yul et al. | |
| 2008/0041399 A1 | 2/2008 | Kriek | |
| 2008/0284289 A1 | 11/2008 | Fisher | |
| 2009/0093671 A1 | 4/2009 | Maloney | |
| 2010/0044372 A1 | 2/2010 | Kournikakis et al. | |
| 2011/0192438 A1 | 8/2011 | Chin et al. | |
| 2012/0215054 A1 | 8/2012 | Rodrigues | |
| 2013/0074895 A1 | 3/2013 | Zimmer et al. | |
| 2014/0163326 A1 | 6/2014 | Forsell | |
| 2014/0212329 A1 | 7/2014 | Veen et al. | |
| 2014/0316455 A1 | 10/2014 | Gnanashanmugam et al. | |
| 2016/0074268 A1 | 3/2016 | Breegi et al. | |

FOREIGN PATENT DOCUMENTS

| | | |
|---|---|---|
| WO | 2005009316 A1 | 2/2005 |
| WO | 2015189541 A1 | 12/2015 |

* cited by examiner

FIG. 2A
FIG. 2B
FIG. 2C
FIG. 2D
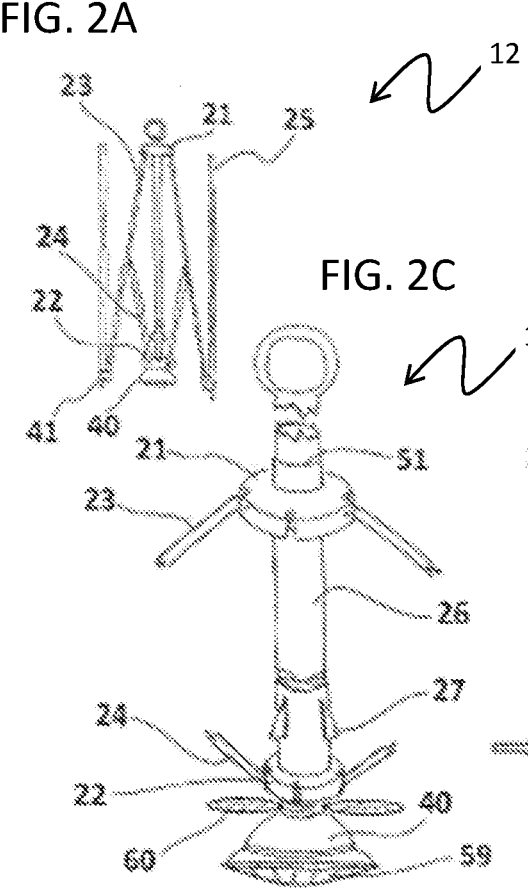
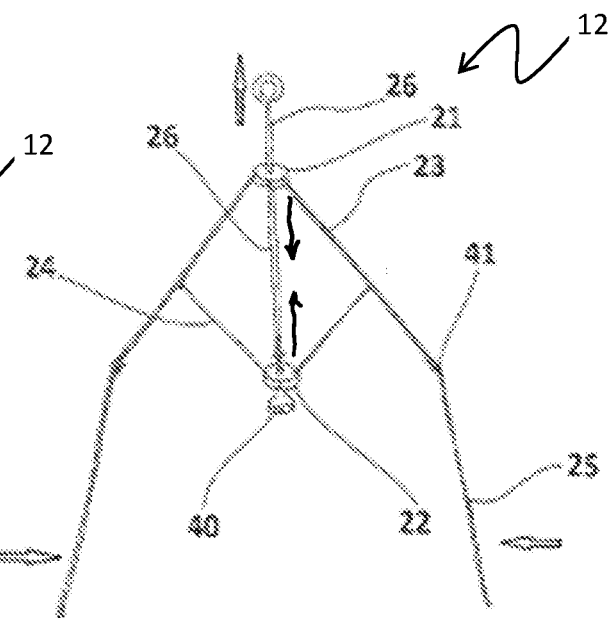
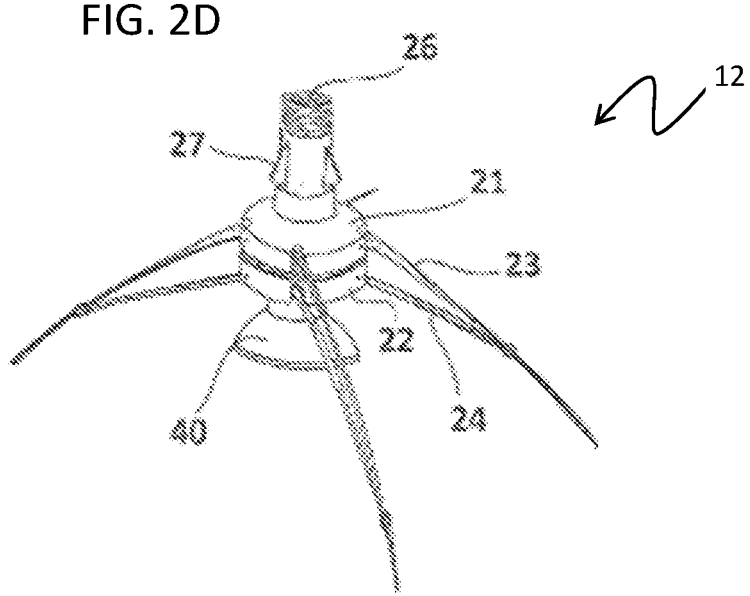

FIG. 7
FIG. 8A
FIG. 8C
FIG. 8B
FIG. 8D
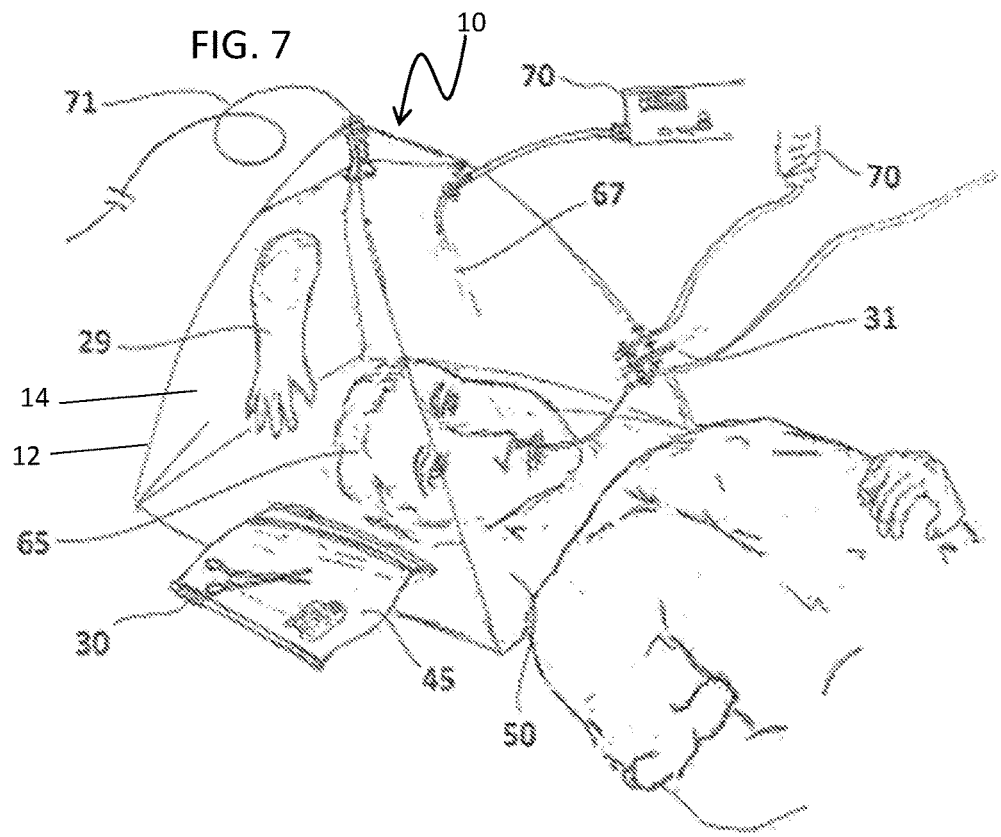
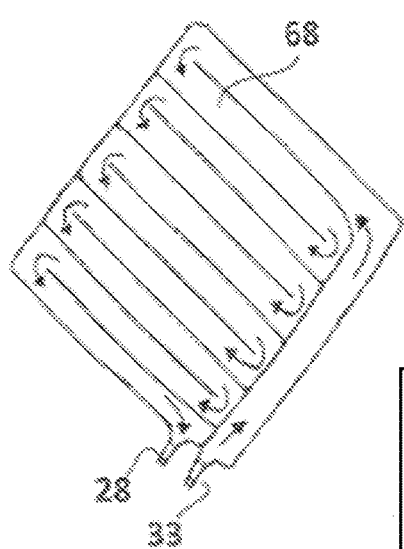
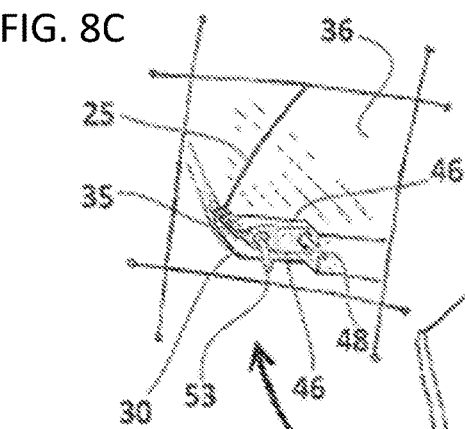
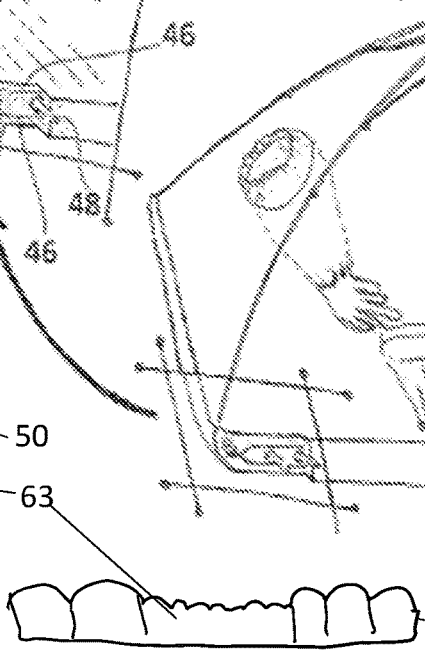
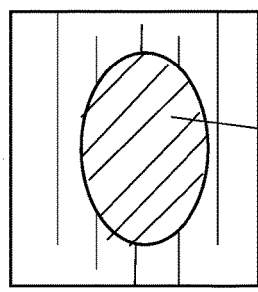

DISPOSABLE INFANT INCUBATOR AND DISPOSABLE CONTAINED MICROENVIRONMENT FOR STATIONARY OR TRANSPORT CASES

CROSS-REFERENCE TO RELATED APPLICATIONS

This application is a 35 U.S.C. § 371 National Phase Entry Application of International Application No. PCT/US2018/016581 filed Feb. 2, 2018, which designates the U.S. and claims benefit under 35 USC § 119(e) of U.S. Provisional Application 62/454,283, filed Feb. 3, 2017, the contents of which are incorporated herein by reference in their entireties.

FIELD OF THE INVENTION

The present invention relates generally to a disposable, expandable, portable, lightweight sterile, environmentally controlled microenvironment that may serve as an infant incubator or other medical, laboratory or industrial field use that requires a medically sterile environment for stationary or transport cases.

BACKGROUND

Presently there is no solution for a disposable, expandable, portable, small, lightweight, inexpensive and optionally sterile microenvironment to serve as a controlled microenvironment housing for an infant incubator. Current infant incubators are one piece, comprising a housing and module controller that provides and supports incubator functionalities. The invention described herein solves these problems.

SUMMARY OF INVENTION

The technology described herein relates to a system, apparatus and methods, for controlling the microenvironment of contained space which can function as a neonatal or infant incubator, also referred to herein as a neonatal intensive care infant incubator ("NICI"). In some embodiments, the neonatal incubator is a disposable neonatal incubator. One aspect of the present invention relates to a controlled environment neonatal infant incubator system comprising a disposable neonatal incubator apparatus which provides a contained space for an infant subject, and a control system module which functions to control the microenvironment in the contained space. The control system module is configured to operate on low voltage, e.g., 12V battery or power source, and thus is suitable for maintaining the microenvironment of the incubator in remote areas where power source is limited, and/or during transport.

Accordingly, one aspect of the technology described herein relates to a disposable neonatal incubator apparatus, which comprises a frame and a disposable housing detachably connected the frame to create a contained space. In some embodiments, the contained space is achieved with a disposable housing which is a disposable canopy and base of the canopy, where the canopy is detachably connected, and in some embodiments, detachably connected (i.e., can be attached and deattached) to a frame structure, where the frame structure is collapsible when the housing is not attached, and is a free standing frame when assembled. Stated another way, the technology and apparatus described herein relates essentially to a "pop-up" disposable neonatal incubator, comprising a disposable housing having walls and a base, and provides an internal surface and an external surface, where the internal surface provides a contained space, and where the external surface can be detachably connected to a disposable or reusable frame, where the frame is a free standing frame and is collapsible when the housing is not attached. Thus the technology and apparatus described herein enables subject care of the infant without the loss of containment integrity and its surrounding environment sterility. In some embodiments, the apparatus enables full or partial containment of the infant subject for treatment, and will address the immediate needs of the patient while being easily carried by the health care providers.

In some embodiments, the frame structure can be disposable or reusable. In embodiments where the frame is reusable, the housing can be detachably connected to the inside of the reusable frame when the frame is in the open or extended configuration. In embodiments where the frame is disposable, the housing can be permanently or detachably connected to the inside or outside of the disposable frame when the frame is in the open or extended configuration.

Another aspect of the present invention relates to a control system module which functions to control the microenvironment of the contained space of the neonatal incubator apparatus, wherein the controller functions to regulate any one or more of the following conditions in the contained space: temperature, humidity, light, gas composition, and sterility, wherein the control system module is in air communication with the contained space by means of one or more tubes which connect to the tube coupling system on one or more inlet ports of the disposable housing. In some embodiments, the control system module comprises a feedback mechanism which can adjust the air flow into the contained space to maintain the microenvironment of the controlled space.

Another aspect of the present invention relates to a control system module for controlling the microenvironment of a contained space of a disposable neonatal infant incubator apparatus, the control system comprising a housing, and any one or more of: (a) a power supply comprising a battery or a voltage converter, or both, (b) a microprocessor connected to the power supply, the microprocessor comprising software for executing a program for controlling one or more of the functions: (i) maintaining temperature within a pre-determined temperature range, (ii) maintaining humidity within a pre-determined humidity range, (iii) maintaining light at within a pre-defined wavelength range, (iv) maintaining the gas composition within a pre-determined range, and (v) maintaining sterility of the air in the contained space, (c) an interface with one or more switches for controlling power to microprocessor, and for controlling any one or more functions (i) to (v); and (d) an outlet port and a tube coupling system configured for air communication with an inlet port on a disposable neonatal infant incubator apparatus.

The technology, apparatus and systems disclosed herein fulfills the need for a sterile disposable, expandable, controllable, small, deployable, portable and practical solution to properly contain and/or support an infant, for example, a premature infant or full term infant, or an infant in need of neonatal intensive care, where the apparatus is adapted to allow any one or a combination of: a sterile environment, application of medication or surgical procedures, administration of food or nutrition, maintenance of temperature and/or humidity at a desired and/or pre-determined level, exposure to phototherapy treatment, e.g., for treatment of jaundice, maintenance of oxygen levels, and/or gas consumption levels, monitoring of the subject in the apparatus, e.g., via cameras, including visual cameras and/or heat sensing cameras etc.

The technology, apparatus and systems described herein addresses a need that is not only required in the secondary care unit, but as a primary measure to contain the neonatal patient as soon as it needed, e.g., to prevent loss of vital signs, tissue/organ functions and costly infections. The technology, apparatus and systems described herein meets these needs, and also can provide a controlled microenvironment to conduct otherwise complex and costly procedures. In addition, the technology, apparatus and systems described herein meets the requirements of incubators for various applications including neonatal incubators. Acting as a neonatal incubator, the apparatus can also sterilely isolated, that is, the contained space is a sterile environment and thus is adapted to allow independent manipulation of different contained items internally without cross-contamination. In some embodiments, the housing comprises one or more internal compartments, where each internal compartment can have its own independently controlled microenvironment. The technology and apparatus described herein meets the requirements of isolated and controlled environments.

Aspects of the present technology relate to a controlled environment neonatal infant incubator system comprising: (a) a neonatal infant incubator apparatus and (b) a control system module, the a neonatal infant incubator apparatus comprises: (i) a frame, e.g., a collapsible frame, and (ii) a disposable housing detachably connected to the frame, the disposable housing comprising a plurality of sidewalls and a base and comprises at least one inlet port with a valve and a tube coupling system, wherein the frame is a collapsible frame, and can be in a collapsed configuration or expanded configuration, and wherein the disposable housing forms a contained space configured for an infant when detachably connected to the frame in the expanded configuration, and (b) the control system module being configured to control the microenvironment of the contained space, the control system module regulating temperature or gas composition, or both in the contained space, and where the control system module includes at least one tube that is in air communication with the contained space via the at least one inlet port of the disposable housing. In some embodiments, both the frame and the housing are disposable.

In some embodiments, the control system module further regulates one or more of humidity, light and sterility in the contained space, for example, regulates the light, e.g., visual light, UV and/or IR light, can introduce sterile air into the contained space and the like. In some embodiments, the control system module is configured to introduce air selected from a group consisting of: heated air, cooled air, humidified air, filtered air, room temperature air, predetermined gas concentrated air, air, and any combination thereof, into the contained space. In some embodiments, the control system module is configured to receive air from the contained space by means of a tube in air communication with the outlet port of the contained space, wherein the control system module is configured to comprise a feedback mechanism for microenvironment of the contained space, where the microenvironment is selected from a group consisting of: temperature, humidity, pressure, airborne particle content, gas concentration, and any combination thereof, where the control system module is configured to maintain the quality of the microenvironment of the contained space in a predetermined value or value range.

In some embodiments, the housing comprises at least one hand port in at least one sidewall, and/or comprises at least one air-locked sleeve in at least one side wall, and/or at least one air-locked infant access door. In some embodiments, the disposable housing further comprises at least one outlet port in at least one sidewall, the outlet port having a valve and a tube coupling system. In some embodiments, at least one sidewall of the housing includes a plurality of layers, and/or the base of the housing includes a plurality of layers, and in some embodiments, at least one sidewall, or the base, or both, are inflatable. In some embodiments, one or more of the plurality of sidewalls comprise a HEPA filter or other air-filtration laminar flow system.

In some embodiments, a fan is present in the contained space, the fan being detachably connected to the frame. In some embodiments, a light source that provides light to the interior of the contained space is present, the light being detachably connected to the frame, for example, a visible light source, or ultraviolet (UV) light source, e.g., for use in phototherapy of the infant subject in the contained space and/or sterilization of the air in the contained space when no infant is in the contained space, or infrared (IR) light source, e.g., for visualizing the infant in the dark. Other light sources include, e.g., white, ultraviolet, blue or infrared light, etc. In some embodiments, a camera is also detachably connected to the frame, the camera monitoring at least one of visible or non-visible spectrum, e.g., and can be operatively connected to the control system module for visual monitoring of the subject, and/or monitoring temperature of the infant subject in the contained space. The housing of the incubator can comprise at least one air-lock sleeve comprises a mechanism at each end that allow the sleeve to be selectively opened and closed at both ends of the sleeve.

In some embodiments, the control system module includes at least one tube that is in air communication with the contained space via the at least one outlet port of the disposable housing. The system control system module can be operatively connected to at least one sensor in the contained space, the sensor configured to monitor any one of: temperature, humidity or gas composition of the air in the contained space.

The control system module as disclosed herein can control the microenvironment of a contained space of a neonatal infant incubator apparatus, the control system comprising a housing for containing any one or more of: a power supply comprising a battery and/or a voltage converter, a microprocessor connected to the power supply, the microprocessor comprising software for executing a program for controlling one or more of the functions: (i) maintaining temperature within a pre-determined temperature range, (ii) maintaining humidity within a pre-determined humidity range, (iii) maintaining light at within a pre-defined wavelength range, (iv) maintaining the gas composition within a pre-determined range, and maintaining sterility of the air in the contained space. The control module system can comprise an interface with one or more switches for controlling power to microprocessor, and for controlling any one or more functions (i) to (v); an outlet port and a tube coupling system configured for air communication with an inlet port on a disposable neonatal infant incubator apparatus.

The control system module can further comprise a display to display the status of the microenvironment of the contained space, where the interface or display is touch screen display. The control system module can further comprise a wireless communication module for controlling any one or more functions (i) to (v) from a remotely. The control system module can include an air circulation system mounted to the housing, the air circulating system comprising an air filter, a heating element, a blower motor and a heat chamber, wherein the blower motor blows air, prior to, or after the air has flowed through the air filter, into the heat chamber, and wherein the heat chamber is connected to the outlet port on the housing, where the outlet port of the housing can include a tube coupling system and be configured for air communication with an inlet port on a neonatal infant incubator apparatus. In some embodiments, the control system module includes an air filter, e.g., a HEPA filter, and in some embodiments, the air filter comprises an internal UV light source. In some embodiments, the battery in the control system module is a 12V battery, and optionally is a replaceable 12V battery or a rechargeable 12V battery.

Another aspect of the technology described herein relates to a process for incubating a neonatal subject, comprising (a) providing a neonatal infant incubator apparatus as disclosed herein, the neonatal infant incubator apparatus including a frame and a disposable housing detachably connected to the frame, the disposable housing comprising a plurality of sidewalls and a base and comprises at least one inlet port with a valve and a tube coupling system, where the frame is a collapsible frame, and can be in a collapsed configuration or expanded configuration, and wherein the disposable housing forms a contained space configured for an infant when detachably connected to the frame in the expanded configuration, (b) providing a control system module as disclosed herein, i.e., providing a control system module configured to control the microenvironment of the contained space, the control system module regulating temperature and gas composition in the contained space, the control system module including at least one tube that is in air communication with the contained space via the at least one inlet port of the disposable housing; and (c) providing and controlling air flow into the contained space with the control system module.

In some embodiments, the technology, apparatus and systems described herein can incorporate any one or more of the following: fluid and gas delivery ports, air-locked bi-directional sleeves and sealing features. In some embodiments, the control system module is capable of introducing gases and/or other fluids into the enclosed contained space, and can include components and features that control the nature, purity, temperature, humidity, light and/or sterility of gases or other materials or procedures introduced into the enclosed, contained space. These components and features can include, but are not limited to, pumps, filters, ultraviolet, ozonizer sterilizers, conduits, couplings, canisters, valves, similar-fluid control devices, electrical controls, direct and indirect lights (white, ultraviolet, blue or infrared light, etc.) and wiring. In some embodiments, the technology, apparatus and system described herein can accommodate sealed entry of a variety of devices and device extensions which can be employed to treat wounds, minimize pain, maintain a sterile environment, and other non-medical functions for the treatment of the neonate in the contained space.

In some embodiments, the technology, apparatus and systems as disclosed herein create a contained space for surgical intervention or other treatment of the neonatal subject in the apparatus. In some embodiments, the disposable housing provides a contained space that is capable of housing a fully introduced subject, e.g., a neonatal subject, or alternatively, can sealing around part of the neonatal subject, e.g., the chest or head, such that the head and upper extremities are contained within the contained space. In some embodiments, the technology, apparatus and systems disclosed herein provides a contained space with a controlled microenvironment around a subject, e.g., where the microenvironment can be sterilized via, for example, by use of an internal or an external source of sterilization, such as, but not limited to, ultraviolet germicidal irradiation and/or ozonizer that circulates treated air within the microenvironment. Thus the closed contained space can be aseptic, sterile environment, which is suitable for a neonatal subject, and/or a surgical environment for performing a surgical procedure on the neonatal subject.

The technology, apparatus and systems as disclosed herein comprises an expandable, frame and a disposable housing, that together, provide a controlled environment, sized and configured by a plurality of ribs or arms of the frame to define a closed contained space and to extend in at least one direction, generally outwardly, with connections and access sleeves for manipulation and handling the infant subject in the contained space.

The technology, apparatus and systems as disclosed herein may accomplish a disposable, expandable microenvironment system comprised of an expandable and collapsible containment frame and housing (canopy), which is sized and configured to support the contained space, to define this closed space (alternately called contained space, containment space, contained volume, or containment volume). It extends in at least one direction generally outwardly from the space to house a work field of full or partial infant subject containment. The space is sized to define an operating or containment field, which consists of a combination of a plurality of ribs or arms, each comprising a lower portion, and upper portion, and a pivot connector interconnecting the lower and upper portions which makes the neonatal infant incubator apparatus. There can be a variety of mechanisms used to achieve this type of expandable neonatal infant incubator apparatus.

In one embodiment, the frame of the neonatal infant incubator apparatus is a collapsible frame and comprises a first hub, a second hub, a plurality of articulated arms coupled to the first hub, a plurality of support arms coupled to both the second hub and the articulated arms, and a flexible canopy carried by the articulated arms. In some embodiments, the frame is collapsed by relative movement of the two hubs away from one another, and deployed by relative movement of the hubs toward one another. The apparatus may further include a releasable locking device that is engaged when the hubs are moved together. In alternative embodiments, the frame is collapsed by relative movement of the two hubs towards one another, and deployed by relative movement of the hubs toward away from one another. The frame may include a shaft connecting the first and second hubs, where one or both of the hubs are movable along the shaft. The articulated arms may be pivotably coupled to the first hub, and the support arms may be pivotably coupled to both the second hub and the articulated arms.

In some embodiments, the housing is attached to the frame, such that when the frame is deployed the housing creates a closed contained space and interior environment. In alternative embodiments, the housing is detachably connected to the frame, so the frame can be reused, and when the frame is deployed, the housing is detachably connected to the inside of the frame to create a contained space.

The housing may be at least in part transparent, and can be made at least in part of a polymeric material. The housing includes a base that forms the bottom of the interior environment, the base may comprise an outer layer that is impervious to fluids, and at least one layer inside of the outer layer that is constructed and arranged to absorb fluids.

The neonatal infant incubator apparatus may include one or more light sources attached, or detachably connected to the frame that provides light to the interior environment. In some embodiments, the light source is a LED light source that is configured to operate using low voltage. The neonatal infant incubator apparatus may further comprise an ultraviolet (UV) light source that is located so as to expose air in the interior environment to UV light. The UV light source may be located outside of the canopy in a volume that is fluidly coupled to the interior environment. The neonatal infant incubator apparatus may include one or more hand ports, also referred to herein as "sleeves" coupled to the housing and extending into the interior, the hand ports sized and shaped to accept the lower end of an arm of a person. The hand ports or sleeves may comprise an elastic cuff that fits tightly over the lower end of the arm. The neonatal infant incubator apparatus may include an air-lock sleeve coupled to the housing, the air-lock sleeve may include mechanisms at each end that allow the sleeve to be selectively opened and closed at both ends of the sleeve.

The neonatal infant incubator apparatus may further include a source of heating or cooling fluid that can be passed through a base of the housing when the apparatus is deployed. The neonatal infant incubator apparatus may further include a reinforcement structure for the housing that is either on or in the housing. The housing may have an outer layer that is impervious to fluids. The neonatal infant incubator apparatus may further include one or more tubes that pass through the housing. The tubes may be for delivery of gas, liquid or mist into the interior environment or contained space, or into a base of the housing.

The technology of the combined system of the neonatal infant incubator apparatus and the control system module is an improvement on prior a prior containment apparatus previously demonstrated by the inventor and disclosed in US Patent application 2016/0074268, which is incorporated herein in its entirety by reference, in that the entire system disclosed herein is mobile, in that the control system module is configured to operate on low voltage, for example, using 12V batteries, e.g., 12V replaceable and/or rechargeable batteries, enabling the system to be used for incubating an infant in areas where power source is limited, and/or for transport of a neonatal infant, where without such a control system module, the microenvironment of the contained space in the neonatal infant incubator apparatus could not be maintained and/or controlled. Further, the neonatal infant incubator apparatus is cost-effective in that the housing is disposable, enabling a new sterile containment space to be generated for each patient, which can be detachably connected to a disposable or reusable frame, providing a cost-effective and safe treatment for infants and preterm babies.

These and other aspects of the technology, methods and systems as described herein will be described in further detail below, in reference to the drawing figures.

BRIEF DESCRIPTION OF THE DRAWINGS

FIG. 1A is an elevation view showing one embodiment of the frame structure, showing the frame structure in the closed configuration (i.e., collapsed) configuration. FIG. 1B is an elevation view of an embodiment of the frame structure shown in FIG. 1A in the extended, or expanded (or open) configuration.

FIGS. 2A-2D show another embodiment of the collapsible frame. FIG. 2A shows one embodiment of the collapsible frame in the closed (collapsed configuration). FIG. 2B shows the frame of FIG. 2A partially erected. FIG. 2C shows details of the frame of FIG. 2A, showing the central shaft with an upper and lower clevis (or hubs). FIG. 2D shows the frame of FIG. 2A in an open configuration (i.e., expanded configuration).

FIG. 3 shows is a perspective view drawing showing one embodiment of the neonatal incubator, with the frame structure in the extended, open position, and where the housing or canopy is detachably connected to the inside of the frame to form the closed contained space. In this embodiment, the housing is detachably connected, and is connected via tunnels at sidewall junctions through which the frame is inserted. In this view, the frame is exterior to the housing and has 4-6 ribs.

FIG. 4A is a view of another embodiment of the frame with the detachably connected canopy, which shows the frame in the interior, and the disposable housing attached, or detachably connected to the outside of the frame. In such an embodiment, both the frame and the housing are disposable. FIG. 4B shows deployment of the one embodiment of the frame shown in FIG. 2A-2B, with the disposable housing detachably connected to the frame in the collapsed configuration.

FIG. 7 is an embodiment of the neonatal incubator apparatus where the neonatal incubator can be used for partial enclosure of the neonatal subject, e.g., the head and, optionally shoulders of the infant.

FIGS. 8A-8D show embodiments of the base of the disposable housing. FIG. 8A shows an embodiment of a mattress or temperature pad for insertion into a base of the housing. Air or water of a pre-defined temperature can be pumped through the temperature pad. FIG. 8B shows a general view of embodiment of the base with a plurality of layers, and FIG. 8C is a detailed view of different layers of the base of the disposable housing, showing more details of the area shown in a box in FIG. 8B. FIG. 8D is an elevation view of an embodiment of a double layered base, or mattress pad, having an indentation or contour that shapes the infant, and a cross sectional view. Shown here is an oval indentation area, other shapes, such as a half circle are encompassed. The area of indentation can in air- and/or fluid communication with the control system module to control temperature, and can be controlled independently or together with the area of the base surrounding the indentation.

DETAILED DESCRIPTION OF THE INVENTION

Figure 4A:
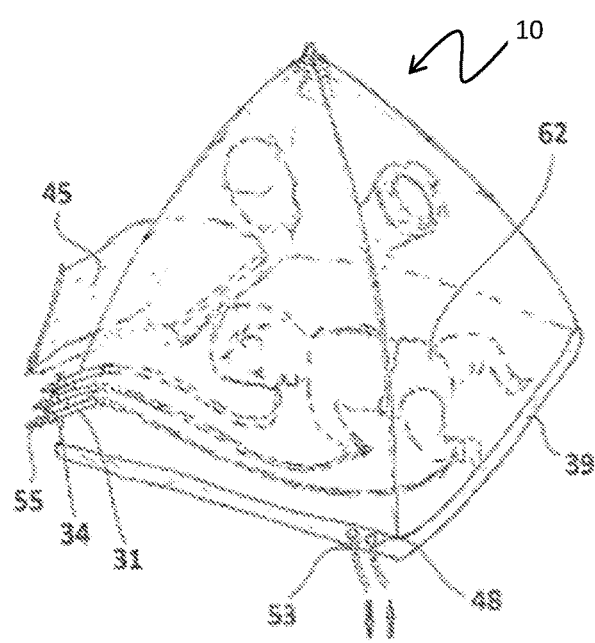
FIGS. 4A-4B show another embodiment of a frame and detachably connected housing to form the contained space of the neonatal incubator.
Figure 9:
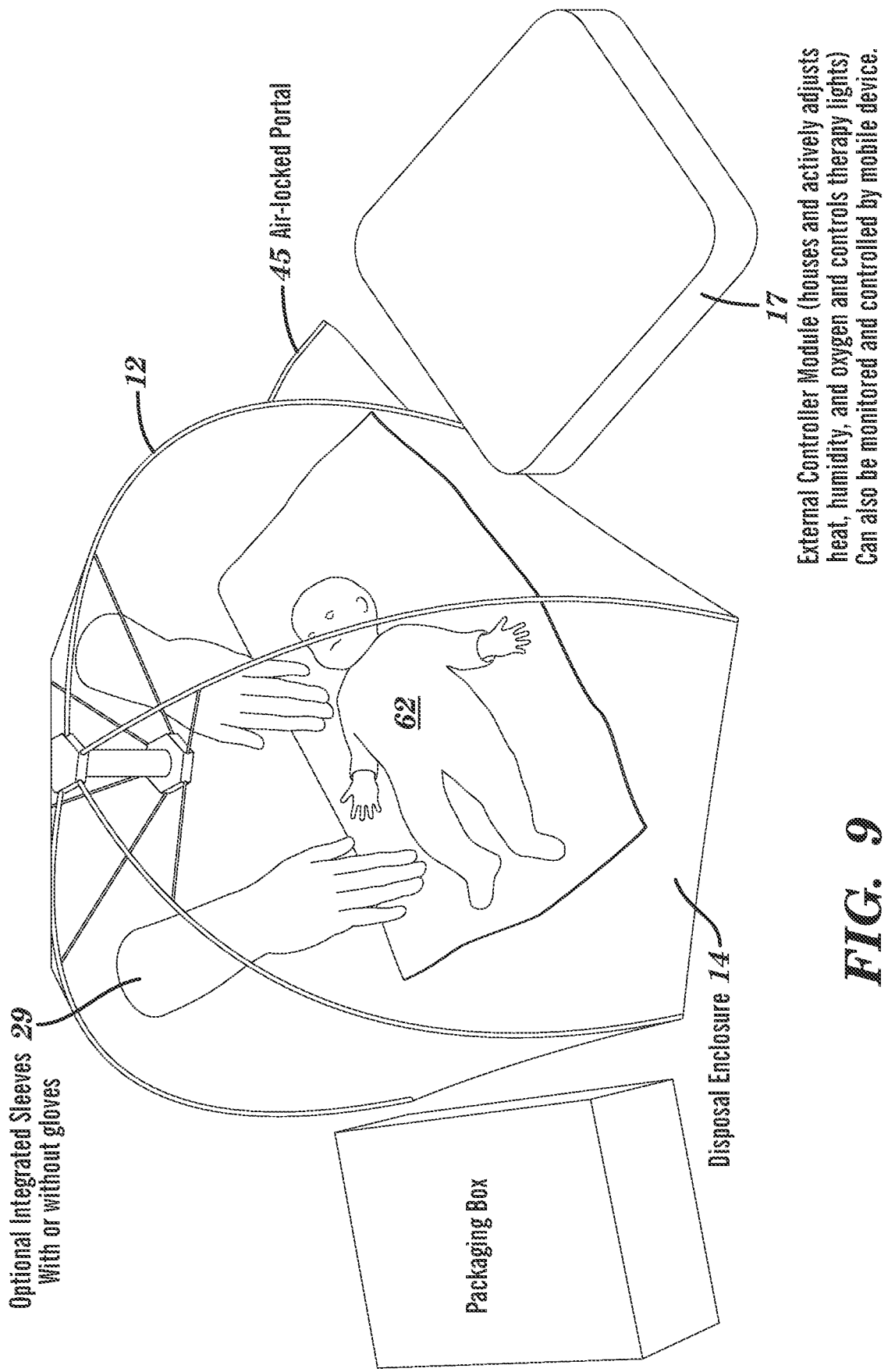
FIG. 9. shows a photograph image of the neonatal incubator apparatus in the expended, open configuration, with a model infant in the contained space, and shows am embodiment of the control system module, and an embodiment of the package for the disposable housing and optionally the frame.
Figure 10:
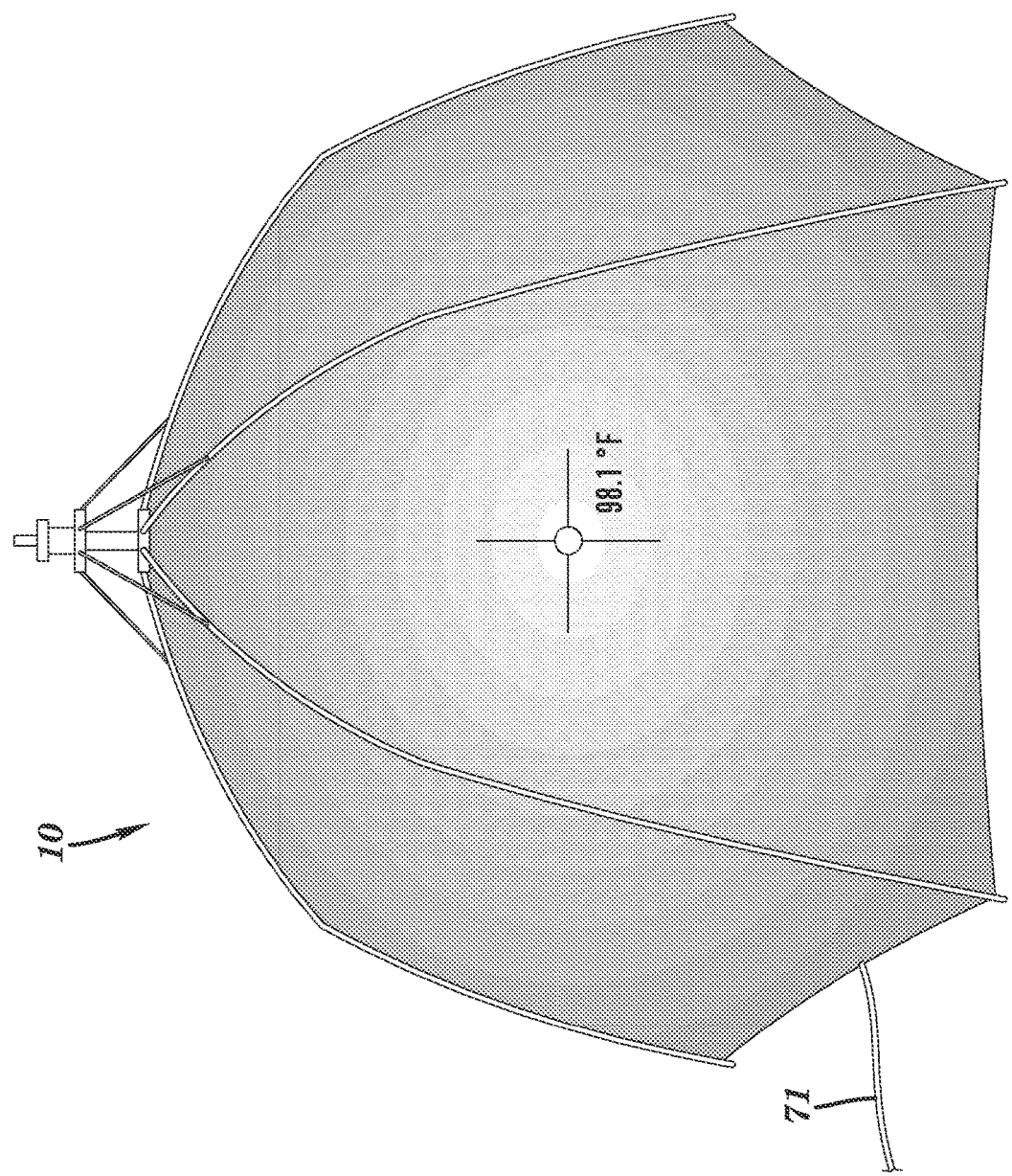
FIG. 10 shows a photograph image from a thermal camera viewing the temperature inside the contained space of the neonatal incubator apparatus.

The technology described herein fulfills a need for a deployable, compact and disposable neonatal incubator apparatus as shown in FIG. 4A and FIG. 9 and methods of use, and systems for maintaining a controlled environment in the neonatal incubator, using a control system module as shown in FIG. 9 and FIG. 10. In accordance with the principles of the technology described herein, this objective is obtained by providing a versatile, portable, and disposable air-tight contained neonatal incubator space.

Figure 12:
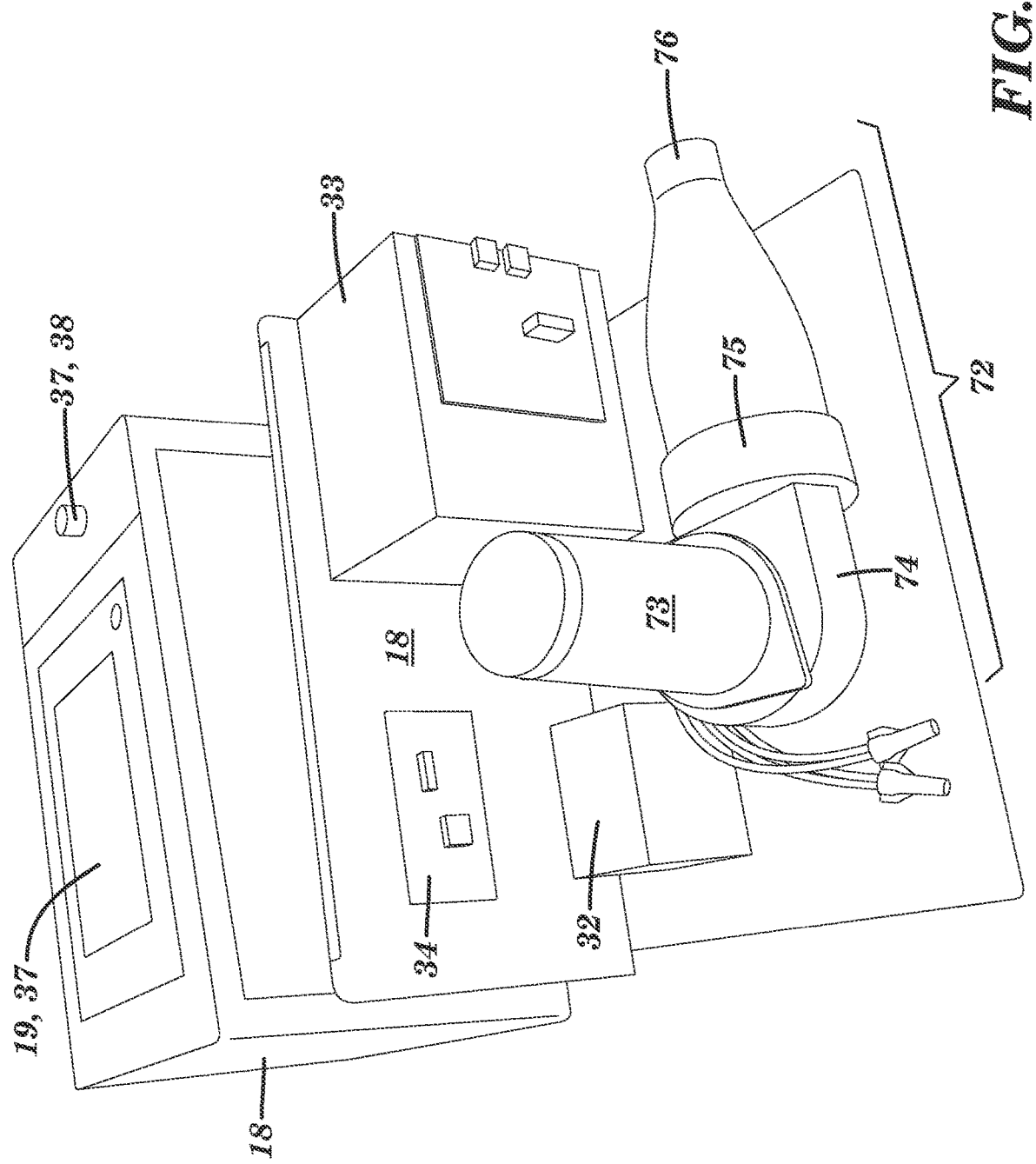
FIG. 12 shows the interior of an embodiment of the control system module, with the housing removed, showing the microprocessor, battery (12V), voltage converter, air circulation system comprising an air filter, heater and/or cooler elements, blower motor, and heat chamber.
Figure 13:
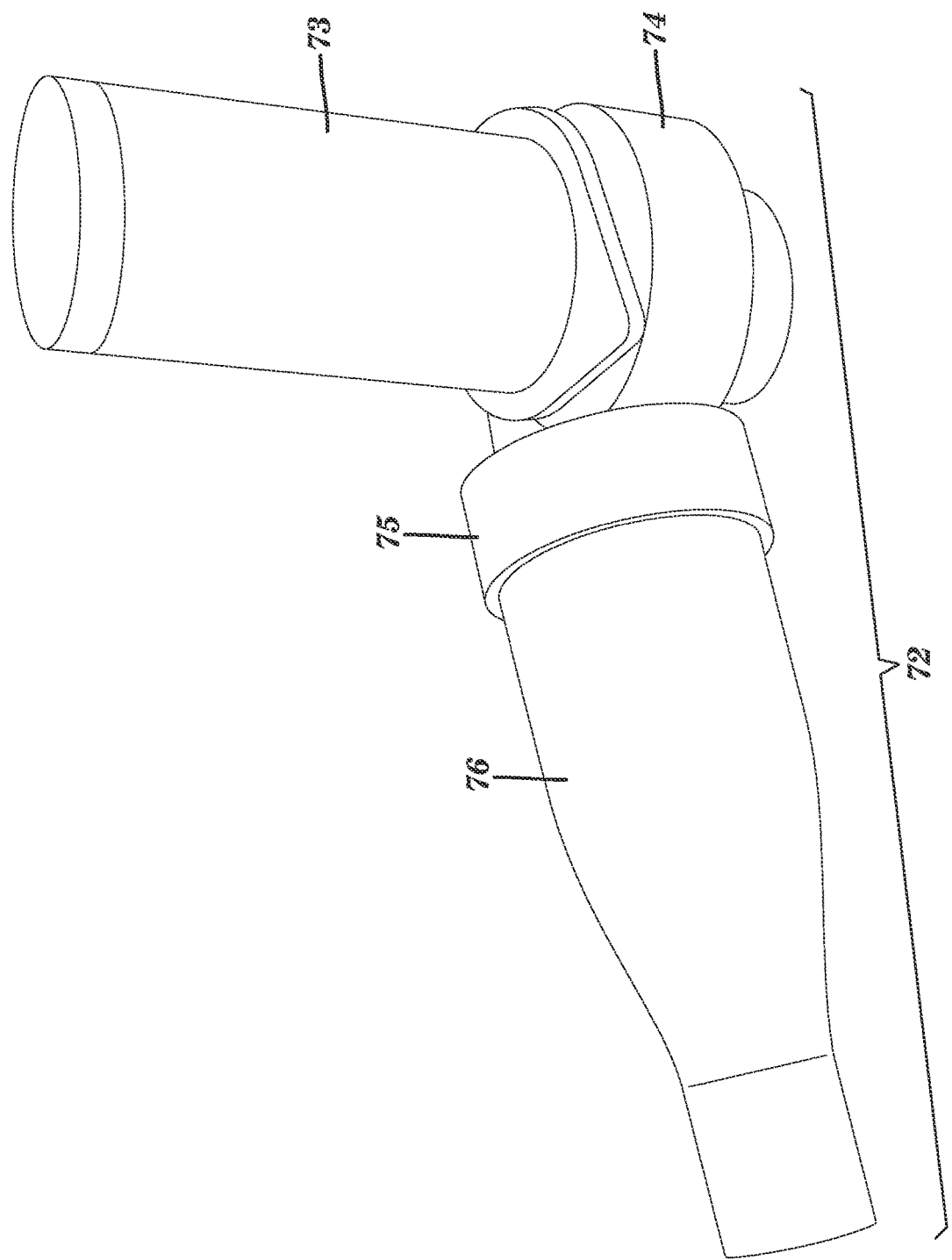
FIG. 13 shows another embodiment of the air circulation system

The technology described herein relates to at least one collapsible frame (see, e.g., FIGS. 1A, 1B, 2A-2D), which can be disposable or reusable, which is used in conjunction with a disposable housing (also referred to herein as a "canopy") to form a contained space (see, e.g., FIGS. 3, 4A and FIG. 5), where the frame in the extended configuration defines a general geometric-shape of the contained space, and where the disposable housing, and optionally, the collapsible frame, is in a sterile sealed package. The package is sized for a portable kit that is easy to carry by individuals (see, e.g., FIG. 12). It is constructed and arranged to be expandable, such that on expansion it forms a closed space (volume), sufficient to house a neonatal subject with the ability to have its own microenvironment. The microenvironment of the contained space is controlled using a control system module (see, e.g., FIGS. 9 and 10), which is in air communication with the contained space via means of tubes connecting an input port, and optionally an output ports of the disposable housing with an output port, and optionally and input port, respectively, of the control system module, thereby controlling and/or regulating any one or more of the following conditions in the contained space: temperature, humidity, light, gas composition, and sterility. The control system module is small and compact and runs on 12V power (using either an internal 12V battery, or external power source which coverts AC to DC, or solar power source), thereby allowing the control system module to be portable and to allow regulation and/or control of the microenvironment of the contained space in remote locations, e.g., where power sources are limited, inaccessible or otherwise not available, or for in-field use, or for transport of a neonatal subject.

Accordingly, the technology described herein relates to an apparatus, system and method to provide a contained space with a controlled microenvironment which can be used as a neonatal intensive care infant incubator ("NICI"). The contained space is achieved with a housing which is a disposable canopy which is detachably connected (i.e., can be attached and deattached), or permanently attached to a frame structure, where the frame structure is collapsible when the housing is not attached. In some embodiments, the apparatus is detachably connected to an electronic controller, which controls function within the contained space of the apparatus.

The housing of the apparatus is a disposable, expandable, and reversible element that defines a contained space, wherein the contained may define a microenvironment which may be used as a neonatal intensive care infant incubator ("NICI"). The housing may also serve as a surgical and biological containment apparatus. The housing is light and portable, and fits many applications. It meets the individual and diverse tasks in medical, laboratory, and industrial fields and uses. When used as NICI, the infant housing maybe disposable to reduce cross-contamination risks and cost of care and maintenance.

The contained space defined by the housing provides an isolated space or volume which may expand outwardly and/or longitudinally to enclose a controlled microenvironment for a neonate to be housed, where the microenvironment of the controlled space is regulated and/or controlled using a control system module, which controls, for example but not limited to, temperature, humidity, phototherapy and a supply of a variety of gases.

The housing is configured to allow visual observation of the neonatal subject in the contained space, as well as to allow manipulation, insertion, and/or removal of items within the interior space of the contained space through one or more particular sleeves while maintaining an isolated and sealed environment as needed. The housing provides either full (e.g., see FIG. 4A and FIG. 9) or partial containment of neonatal subjects (e.g., see FIG. 7) within the contained space.

As disclosed herein, one aspect of the technology described herein relates to a control system module (also referred to herein as a "module"), which is reusable. In some embodiments, the control system module is compact. In some embodiments, the control system module has an optional wireless communications module for remote monitoring. In some embodiments, the control system module is designed to run on a rechargeable 12V power source, thus allowing the apparatus disclosed herein to be used as a portable incubator, either set up at a desired location, or alternatively a vessel for containing a neonatal subject during transport. In some embodiments, the control system module can be operated by the user at the site of the housing, or alternatively, at a site remote to the housing, e.g., where it is operated by a user via wireless connection to an interface. In some embodiments, the control system module can be used to monitor, or control or change any one or combination of the following microenvironments: heat, cold, humidity, phototherapy, and gases in addition to camera monitoring. In some embodiments, the control system module, which provides different functionalities to support the controlled microenvironment of the contained space, may be connected to the housing, directly or indirectly through tubes, wires and/or wireless connectors.

These and other features and examples will be described in further detail below. The embodiments described herein are provided for exemplary purposes only and should not be interpreted as limiting the scope of this invention as set forth in the claims. The apparatus as disclosed herein is now further described with reference to the figures.

I. Neonatal Infant Incubator Apparatus:

IA. Collapsible Frame:

One aspect of the technology described herein relates to a neonatal infant incubator apparatus 10 comprising at least one collapsible frame 12 (see, e.g., FIGS. 1A, 1B, 2A-2D), which can be disposable or reusable, which is used in conjunction with a disposable housing 14 (also referred to herein as a "canopy") to form a contained space 16 (see, e.g., FIGS. 3, 4A and FIG. 5), where the frame 12 in the extended configuration defines a general geometric-shape of the contained space 16.

Figure 1A:
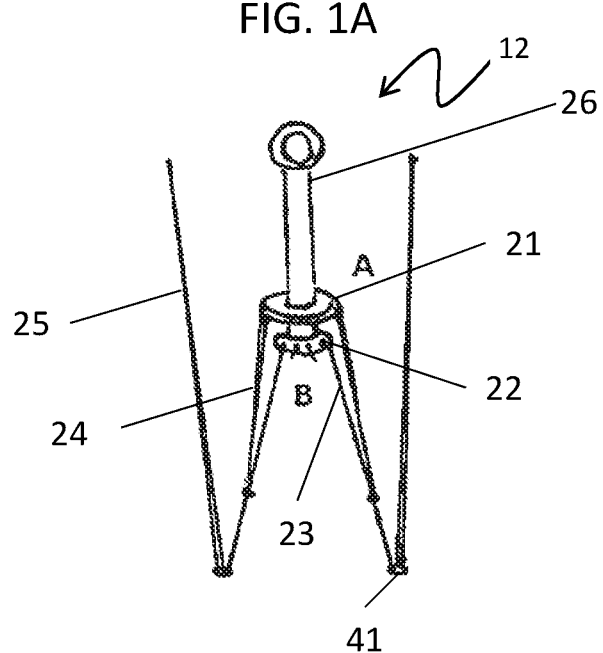
FIG. 1A-1B shows one embodiment of the frame structure in the open and closed configuration.
Figure 1B:
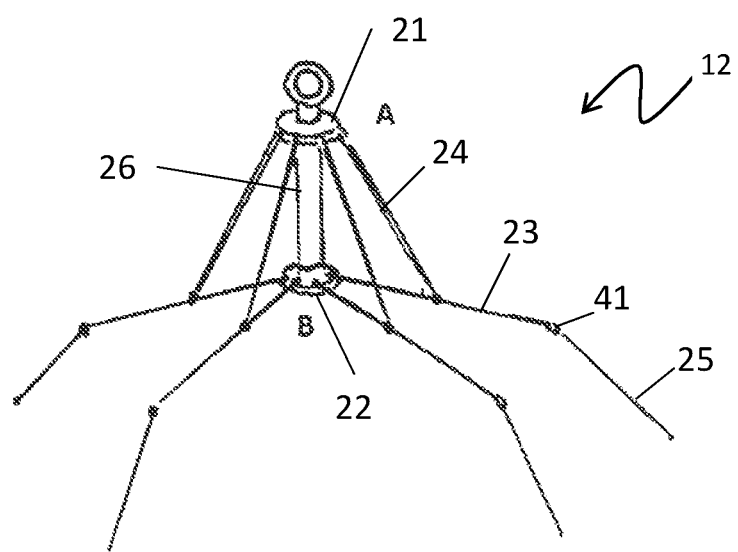

FIG. 1A-1B shows one embodiment of a collapsible frame 12. FIG. 1A shows an embodiment of the frame 12 in the collapsed configuration (i.e., closed configuration), and FIG. 2 shows an embodiment of the same frame in the open, expanded configuration, where the frame 12 is a free standing structure in this configuration. In such an embodiment, the frame includes a combination of a plurality of ribs each comprising a lower portion 25, and upper portion 23, and a pivot connector 41 interconnecting the lower 25 and upper portions 23, as best seen in FIGS. 1A and 1B. There can be a variety of mechanisms used to achieve this type of expandable frame structure for use in the desired applications.\. Referring to FIG. 1A, a frame 12 can comprise a first hub A 21, a second hub B 22, and a central shaft 26, a plurality of articulated arms coupled to the second (lower) hub 22, a plurality of support short arms 24 coupled to both the first (upper) hub 21 and the articulated arms. In this embodiment and in contrast to the frame shown in FIGS. 2A-2D, the frame 12 collapses or closes by relative movement of the first hub A 21 toward second hub B 22 (or vice versa), and can be deployed by moving the two hubs 21 and 22 away from one another, as best seen in FIGS. 1A and 1B. When the frame is deployed, and a disposable housing is detachably connected 10, the canopy creates an expanded closed containment space 16 where the microenvironment can be controlled, as best seen in FIG. 3A. The articulated arms carry a flexible, disposable canopy or housing 14.

The frame 12 may include a central shaft 26 connecting the first hub A 21 and second hub B 22, where one or both of the hubs, hub A 21, hub B 22, are movable along the shaft. The articulated arms may be pivotably coupled to the second hub B 22, and the support short arms 24 may be pivotably coupled to both the first hub A 22 and the upper portion 23 of the articulated arms. In some embodiments, the frame 12 may further include a releasable locking device 27 that is engaged when the hubs, first hub A 21 and second hub B 22, are moved together.

Figure 4B:
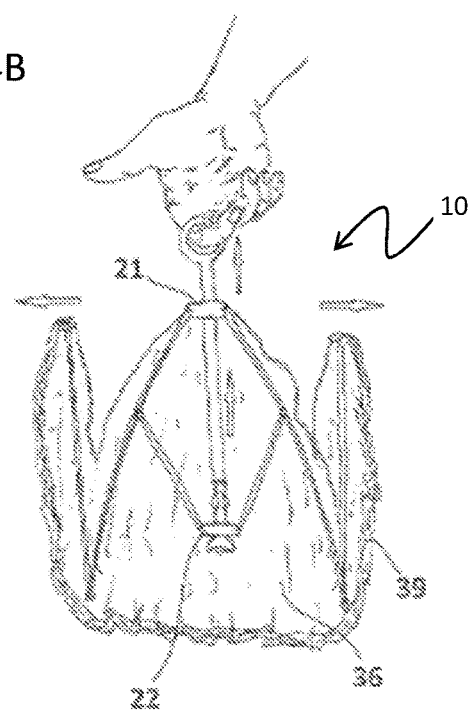

FIG. 2A-2D show another embodiment of a collapsible frame, including a plurality of articulated arms (also referred to herein as "ribs") pivoted at their upper ends to an upper hub 21 providing a given final structure shape. At points spaced downwardly from their upper ends, each arm has pivoted thereto a radial stay member extending inwardly of the dome 24 to be pivoted to a lower hub 22. The upper hub 21 includes a central opening 51 to slide upwardly a central shaft 26, which is connected to the lower hub 22. The lower hub 22 is fixed to the central shaft or rod 26 which protrudes upwardly and passes through upper hub 21. In this embodiment, in contrast to the mechanism shown in FIGS. 1A-1B, the central shaft 26 is pulled upwardly manually or mechanically to deploy and erect the collapsed frame (see FIG. 2B and FIG. 4B). Referring to FIG. 4B, the upper hub 21 will stop the upward movement of the lower hub 22, and the upper hub 21 can lock into place with a spring-lock mechanism 27 as it moves down the central shaft 26. In some embodiments, the central shaft 26 comprises a spring-lock mechanism 27 which is fixed toward the lower part of the central shaft 26. It latches when the lower hub 22 reaches the upper hub 21 and the latches 27 pass the opening 51 of the upper hub 21 and expand outwardly and sit on the upper surface of the upper hub 21. Latches 27 can be pushed inward to allow the opening 51 of the upper hub 21 to pass by, thereby allowing hubs 21 and 22 to be pushed apart to collapse the frame.

In some embodiments, each articulated arm (or rib) of the frame 12 is comprised of an elongated lower section 25, which can be relatively flexible. The upper end of the lower section 25 is pivotably connected at joint 41 to an upper section 23, which is pivoted to the upper hub 21, and is relatively flexible and resilient so that the upper portions of the ribs 23 conform to the shape of the canopy material forming the overall shape of the contained space 16 of the apparatus 10. In the embodiment of the frame 12 shown in FIG. 2A-2C, the collapsible frame 12 is deployed by pulling up on the two rings while also pulling them apart.

Figure 6:
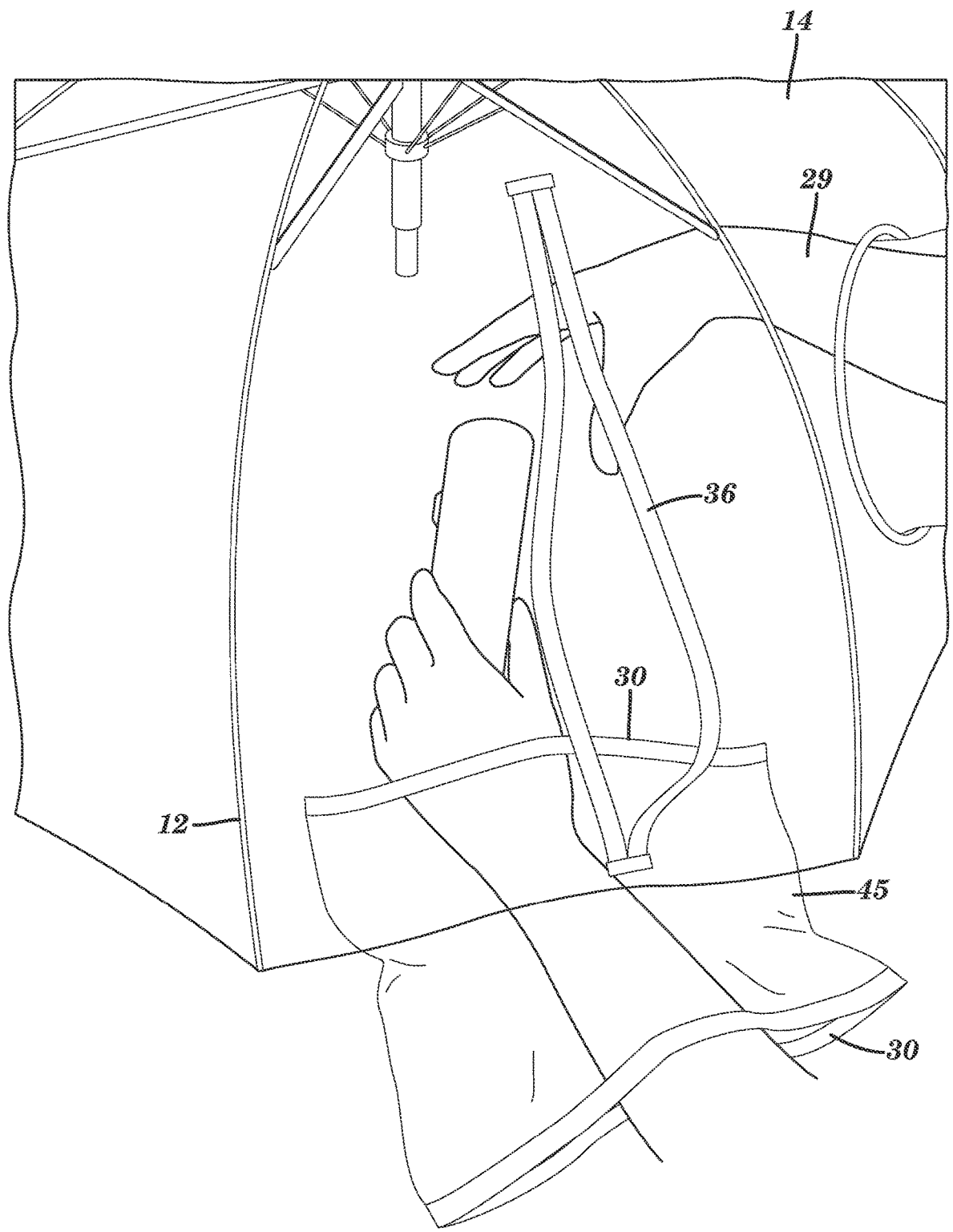
FIG. 6 is a photograph of an embodiment of the neonatal incubator apparatus where the frame in the expanded configuration with the canopy detachably connected to the outside, and access to the contained space via either the air-lock sleeve or the air-lock patient access door.
Figure 14:
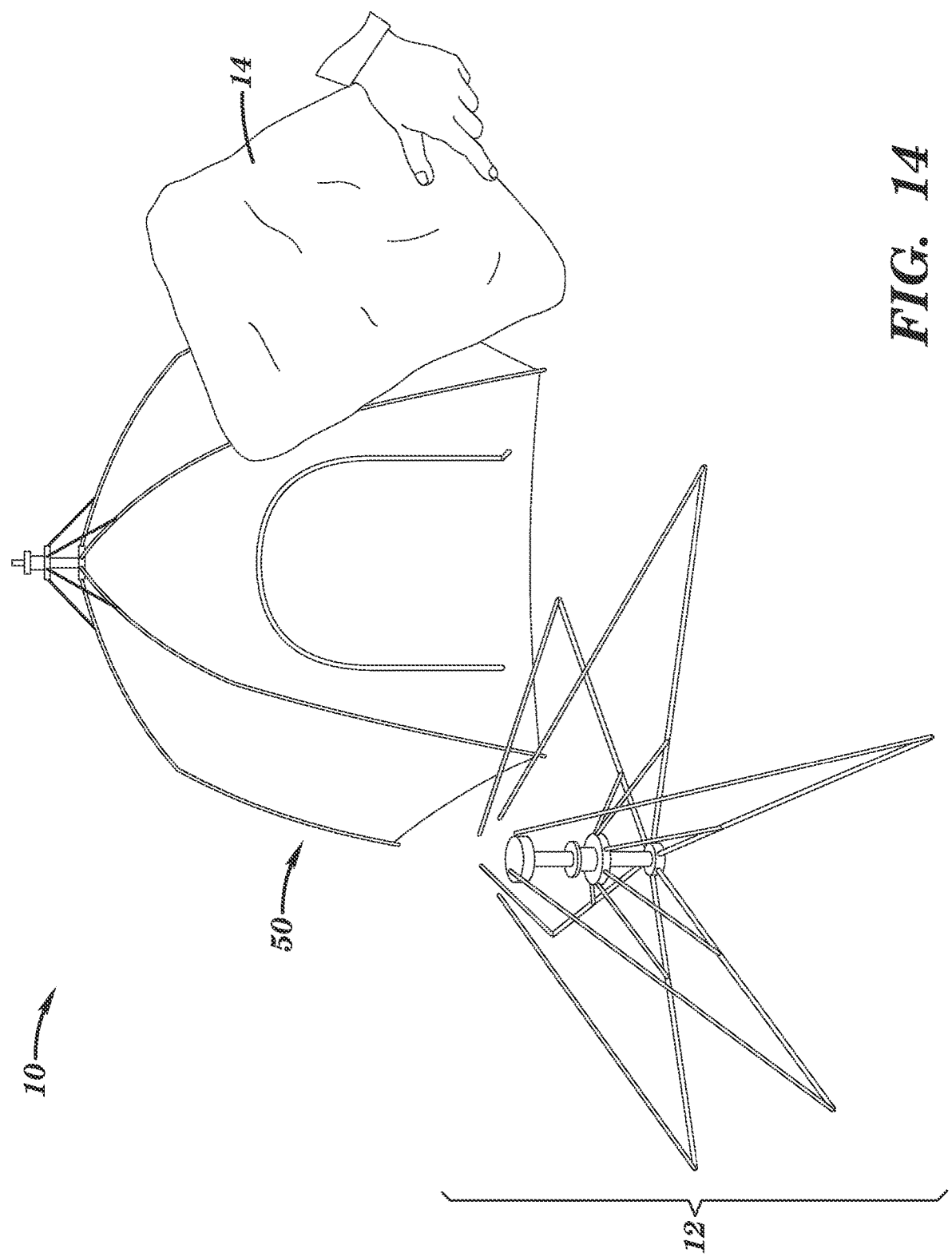
FIG. 14 is a photograph of the disposable housing in the folded compact form, which is not attached to the frame, a frame in a collapsed configuration, and the neonatal incubator with the frame on the exterior of the detachably connected disposable housing. In this embodiment, the base of the disposable housing is double layered and inflatable.

The general construction of the collapsible frame 12 may be comprised of a metal or polymeric rib structure (e.g., see FIG. 6, FIG. 9 and FIG. 14). Advantageously, the articulated arms or ribs and of the frame 12 can be extruded polymeric tubing or rods, or metal tubing or rods. The hub members 21 and 22 can be molded from polymeric material or are metal, as are all of the pivotal connector members 41 of the frame 12. In some embodiments each ribs, or arms of the frame are a single unit (i.e., one piece) and are flexible, such that when the housing is detachably connected to the frame, the arms provide tension to provide a contained space.

I B: Disposable Housing of the Neonatal Infant Incubator Apparatus

As discussed herein, one aspect of the technology described herein relates to a disposable neonatal incubator apparatus 10, which comprises a frame 12 and a disposable housing 14 detachably connected the frame to create a contained space 16 with a controlled microenvironment. In some embodiments, as illustrated by the embodiment shown in FIG. 3, the frame 12 is reusable, and the housing 14 is detachably connected to the inside of the frame 12, such that the frame 12 when in the expanded configuration, exists as an exterior support of the housing to generate the contained space 16, and after the incubator has been used by a subject, the disposable housing 14 can be detached from the frame and discarded, and the frame 12 can be reused with a new sterile disposable housing 14. In such an embodiment, tunnels 20 or other attachment means, such, e.g., as hooks, rings, tabs with grommets, pair of ties, or sleeves, or hook and loop type fasteners (e.g. Velcro® hook and loop fastening materials, or other mechanical fasteners, attached to the outside of the housing, e.g., at sidewalls junctions 38, are used to attach the housing 16 the articular arms 23 and 25 of the frame. In some embodiments, the articulated arms 23 and 25 of the frame are passed through one or more tunnels 20 on the housing to secure the housing to the external frame 12. When the housing 14 is detachably connected in this manner to the exterior frame 12, the flexible articulated arms of the frame bend are and held in a state of compression, thereby the housing 14 is distended in a state of tension by the frame in the open configuration. In some embodiments, the housing comprises one, or two or 3 or 4, or more than 4 tunnels 20 for each arm of the frame 12. In some embodiments, the housing can also comprise a fastening means into which the lower end of each arm 25 of the frame can be inserted, such fastening means includes a tab with grommets or a ring, which is attached to the base 50 of the housing, e.g., at the base-wall junction, or the seam 39 where the based and sidewalls of the housing connect, to connect to the bottom of each arm. In this embodiment, the contained space 16 is achieved when the disposable housing 14 (which is a disposable canopy and base of the canopy 50 provided in a sterile package, see FIG. 14) is detachably connected (i.e., can be attached and detached) to a frame 12 in the open configuration, where the frame structure is collapsible when the housing is not attached.

In an alternative embodiment, as illustrated by the embodiment in FIG. 4A, both the frame 12 and the housing 14 are disposable, and the housing 14 is detachably connected to the outside of the frame 12, such that when frame is in the extended into open configuration, the frame 12 is in the interior of the contained space, and provides an internal support for the housing 14. In such an embodiment, the housing can be attached to the frame in the collapsed configuration, such that when the frame 12 is deployed into its open configuration, the frame and attached housing 14 immediately form the contained space 16 (e.g., see FIG. 4B).

In all aspects of the technology described herein, the disposable neonatal incubator apparatus 10 is an expandable and collapsible closed system, transparent, air and liquid impermeable space; an expandable and collapsible contained apparatus adapted to be erected in the field or where needed from a collapsed compacted form into an expanded form for incubation of, and/or treating a neonatal subject or performing a task; and/or isolating, transporting and treating a neonatal subject.

In some embodiments, where the frame 12 is reusable and the housing 14 is disposable, the frame is deployed from the collapsed configuration into the open configuration, and the housing, provided in a sterile compact package (see FIG. 14) is opened and then detachably connected or attached to the open frame 12 structure. In some embodiments, where the frame 12 and the housing 14 are disposable, the disposable neonatal incubator apparatus 10 extends from at least one direction generally outwardly from a collapsible packaged (FIG. 4B) to house a contained space 16. The contained space 16 has sufficient room for full containment of a neonatal subject 62 (FIG. 4A) or partial containment of a neonatal subject 65 (FIG. 7).

Figure 3:
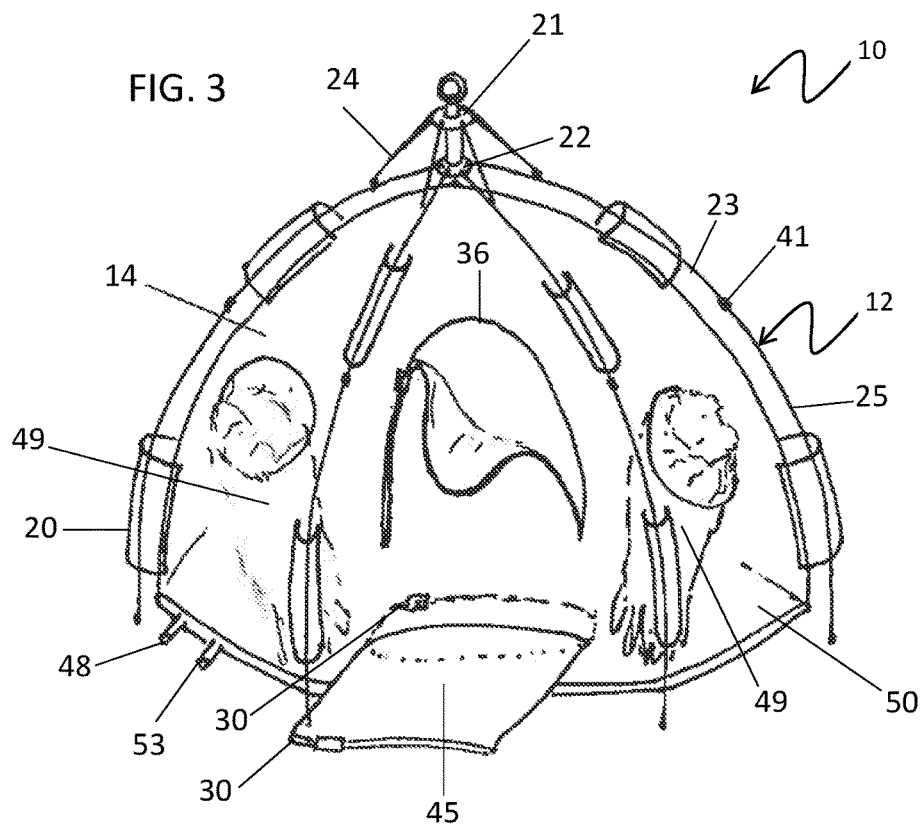
FIG. 3 shows an embodiment of a frame and detachably connected housing to form the contained space of the neonatal incubator.

The housing 16 maybe sized and configured by a plurality of ribs or arms that define a closed contained space 16 and to extend in at least one direction, generally outwardly, with connections and access sleeves for manipulation and handling objects and things in the contained space. In some embodiments, the containment space (i.e., dome) 16, consists of an at least partially transparent (see through) polymeric canopy of high transparency and strength. In some embodiments, where the frame is external, the canopy has strength to be distended in a state of tension by the attachment to frame in the open configuration (FIG. 3). In some embodiments, where the frame is internal, the housing 14 tightly covers the ribbed frame structure (FIG. 4A) to form a contained space 16. In such an embodiment, the housing covers tightly, when erected, the volume of the frame 12 from all directions (FIG. 4A). The housing 14 typically has a plurality of side walls 37, with the junctions 38 of each sidewall typically aligning with each arm of the frame 12. The contained space 16 is sterile, and provides a space for a controlled microenvironment for containing a neonatal subject. In some embodiments, the housing or canopy 14 may consist of liquid, fog and glare repellent polymeric surface material. In some embodiments, the housing 14 or canopy is made of transparent polymeric material, and optionally can comprise an integrated reinforcing fiber-based net, or may be reinforced by spaced fibers permanently attached to or within the transparent housing material 14. In all aspect, the housing comprises a complete floor portion or base 50, which is connected to the sidewalls 37 of the housing through connecting edge or seam 39.

In some embodiments, the housing 14 can comprise one or more hand ports 29. The hand ports 29 connected outwardly to openings in the side of the canopy, with sealing elastic cuffs 43 to form a tight closure around the operator's arms. In some embodiments, inwardly, the other free ends of the hand ports 29 can terminate with a tight seal around the user's wrist, 52, and in alternative embodiments, the hand ports 29 can end in gloved formation 49. A completely sealed and loosely connected inner diaphragm can be positioned at a wrist elastic region 52. The hand ports, also referred to as "hand sleeves" herein are tubular and openly connect outwardly to the surface of the housing 44, with an elastic edged-curtain 43 to form a tight closure around the upper part of the operator arms or any other object. These polymeric hand ports 29 can be modified and used to handle and manipulate the infant subject inside the contained space without having direct physical contact between the operator's hands and the inner surfaces, objects or space of the contained space.

In some embodiments, the housing 14 comprises one or more two-sided opening delivery (pass through) air-lock sleeves 45 which are connected to the surface of the canopy; with ends consisting of an air-lock closing system, e.g., a closing zipper, Velcro® (hook and loop fastening materials) or other types of interlocking and sealing mechanisms 30, to close both ends of the sleeve 45, both outwardly and inwardly. Thus the sleeves act as air-locks. These air-locked sleeves 45 allow controlled access to the inside and the outside of the neonatal incubator apparatus, while maintaining the controlled environment of the contained space 16. In some embodiments, the housing may also comprise sleeves with smaller ports, e.g. to deliver or provide an access path for entry of devices such as scopes. In some embodiments, the housing can comprise input ports for introduction of fluids and the like, e.g., to adjust humidity and the like.

In some embodiments, the housing 14 comprises one or more air-locked patient access door 36 (see FIG. 3 and FIG. 6), comprising an air-lock closing system, e.g., a closing zipper, Velcro® (hook and loop fastening materials) or other types of interlocking and sealing mechanisms 30, to insert and remove an infant subject from the contained space 16.

In some embodiments, one side of the housing surface (typically the outside) can comprise one or more controlled flow mechanisms 54 (e.g., valves) for access tubes 31 passing through the canopy for fluid, mist 67, filtered or sterilized air, electrical cords 71 and other such supply or device needs 70, with couplings 55 providing connections between the outside and the inside of the apparatus. One tube can have a small bidirectional air flow filter 70 connected to a tube to inflate the containment volume or to suction air out or to provide certain gases.

In some embodiments, at least one or all sidewall of the housing 16 can be single or double layered. In some embodiments, a double layered housing can be inflatable, e.g., filled with air, e.g., for insulation purposes. In some embodiments, the housing may be double-walled and filled with gas (e.g., air) or fluid, wherein said fluid may be static or dynamic, to provide support and/or thermal control to the contained space 16. In some embodiments, the air and/or fluid can be in air and/or fluid communication with the control system module 17 for maintaining and/or control the temperature of the contained space within a pre-defined temperature range. In such an embodiment, the housing which is double layered has a port for input of air and/or output of air in the outer layer of the double layered housing for inflating the housing. In some embodiments, a double layered housing has an input and/or output port, which are in air communication with the control system module 17 for maintaining and/or control the temperature of the contained space within a pre-defined temperature range.

The housing base 50 can have a continuous base surface connected 39 to the downward end of the housing sidewalls 37, which will provide a closed system. Base 50 can be made of double polymeric sheet or layers of surgical absorbent drape materials 35, 46. Double polymeric sheets 46 are sealed completely around the edges 39, and in some embodiments, the base 50 can be fully or partially filled with air, i.e., inflated. In some embodiments, the base 50 can be configured to allow insertion and to enclose a mattress 68 of zigzag tubes for circulating air or fluid to create a temperature controlled mattress with two simple in and out valves 48, 53, which can be air- or fluidly connected to the control system module 17. In some embodiments, the base comprises a plurality of layers, such as two layers 46, 46 (see FIG. 8C), which function the same as the removable mattress 68, and can be inflated, including containing zig-zag connections for circulating air/and fluid in the base 50 (see FIG. 14). In some embodiments, this removable air or fluid filled mattress 68 (see FIG. 8A), or internal cushion of the base 50 (see FIG. 8C) can cushion and support an infant located inside the apparatus and can also provide heat insulation and be used to control the temperature of the contained space within a pre-defined temperature range. The base 50, or removable mattress 68 can be inflated to provide a contoured surface (see FIG. 8D), having an inflated circumference/edges of the base, with an area of indentation having less or no inflation (e.g., an oval, half circle, or similar shape to hug or surround the infant), which centrally positioned in the base 50 or the removable mattress 68 for placement of the infant, to prevent the baby from rolling over. Other embodiments of a contoured surface of the base 50 include a ridge or lip, or other protruding form from the surface of the base 50 in an oval, curved shape or half oval, to surround the baby to prevent the baby from rolling over. In some embodiments, there can be an air filter 28 (e.g., a HEPA filter) fixed on the side of one of the canopy surfaces to provide filtered air to the dome if needed. In some embodiments, a removable mattress 68 comprises a vibration device operatively connected to the control system module and configured to vibrate intermittently, of a sufficient amount and frequency, for example, to stimulate an infant in the contained space to breathe, and can be used for example, for the treatment of an infant with apnea and/or to prevent sudden infant death syndrome (SIDS), and/or to teach an infant to breathe. Use of a removable mattress 68 with a vibration device can be coupled with an increased oxygen concentration in the contained space, and can be operatively controlled by the control system module for the treatment of an infant with apnea and/or to prevent an infant at risk of sudden infant death syndrome (SIDS).

In some embodiments, detachably connected to the frame 12, there can be a light source 40 of any wave length that can be configured to be operated by the control system module 17, or outer source of power 71, to illuminate the contained space or to provide ultraviolet (UV), blue or infrared light within the contained space. In some embodiments, the light source is a plurality of LEDs or a LED light source that is configured to operate using low voltage. In some embodiments, where the frame is exterior to the housing (see FIG. 3), the light source can be detachably connected to an arm, or lower hub 22 of the frame 12, and inserted through an air-locked port in the housing, or alternatively shine through the housing and into the inner space of contained space 16. In alternative embodiments, where the frame is internal (see. FIG. 4A), a light source 40 can be connected to the bottom of a lower hub 22, facing the inner space of the contained space 16, or alternatively, a plurality of LEDs can be detachably connected, or permanently attached to the interior of the frame. In some embodiments, a light source 40, such as UV, may have a removable shield 59 placed in front of it to prevent direct exposure of the infant subject or patient to the light, but it will allow direct contact and circulation of the contained air within the space of the embodiment. In some embodiments, the light is used for phototherapy of the infant subject, e.g., for treatment of a subject with jaundice and the like. In some embodiments, the light is operatively connected to the control system module, where the operation of the light, e.g., turning on, off, duration of exposure, wavelength exposure etc. can be controlled by the user via the control system module. In some embodiments, the light is blue light for phototherapy, and is operated via the control system module and has a feedback mechanism to ensure that the blue light does not turn on unless the subject is wearing eye protection.

In some embodiments, the neonatal infant incubator device 10 can also comprise a small fan 60, to circulate the air within the interior space of the contained space 16. In some embodiments, similar to the attachment of the light, where the where the frame is exterior to the housing (see FIG. 3), the fan 60 can be detachably connected to an arm, or lower hub 22 of the frame 12, and inserted through an air-locked port in the housing. In alternative embodiments, where the frame is internal (see. FIG. 4A), a fan 60 can be connected to the bottom of a lower hub 22, facing the inner space of the contained space 16.

In some embodiments, the neonatal infant incubator device 10 further comprises a camera, which can be used to monitor visible and non-visible spectrum, e.g., infra-red. Similar to the light and fans, the camera is reusable, and in some embodiments, where the frame is exterior to the housing (see FIG. 3), the camera can be detachably connected to an arm, or lower hub 22 of the frame 12, and the entire camera inserted through an air-locked port in the housing, or alternatively the lens of the camera, or an adapter to the lens, can be inserted through an air-locked port in the housing into the contained space. In some embodiments, the lens of the camera looks through a window in the housing into the inner space of contained space 16. In alternative embodiments, where the frame is internal (see. FIG. 4A), a camera 40 can be connected to the bottom of a lower hub 22 of the frame 12, facing the inner space of the contained space 16. In some embodiments, the camera can view the subject in normal light, in the dark (e.g., night vision and or infra-red spectrum), as well as viewing the temperature of the subject, e.g., monitoring an infant subject to determine if the subject is hyperthermic or hypothermic. In some embodiments, the camera is operatively controlled by the control system module 17, where an image obtained from the camera can be viewed on a display 19 of the control system module, or alternatively, on a remote device by wireless communication with the control system module.

In some embodiments, the housing 14 is made of a disposable material can be in a collapsed compacted form that, when it is opened and detachably connected to the reusable frame 12 in the expanded configuration, provides a containment space 16 for placement of a neonatal subject, or part of a neonatal subject, e.g., the head and/or shoulders (see FIG. 9 and FIG. 7).

One aspect of the technology described herein is that it provides an expandable disposable housing 14 that defines a contained space 16 with a controlled microenvironment, where the microenvironment is controlled via fluid and/or air communication with a control system module 17. The housing 14 may include a membrane/canopy comprising single or double layers. The canopy may extend in at least one direction generally outwardly from the contained space to create a contained space for full 62 or partial subject 65 containment of the infant.

The housing 14 may be at least in part transparent and may be at least of made of one or more layers. The canopy may be made at least in part of a polymeric material. The canopy may include a base 50 that forms the bottom of the interior closed microenvironment of the contained space. The base 50 may comprise an outer layer that is impervious to fluids 46, and at least one layer 35 inside of the outer layer that is constructed and arranged to absorb fluids. The base 50 may include least two layers 46, 46 (see FIG. 8C), which can allow insertion of a mattress 68 (see FIG. 8A), or where the layers between two 46 layers, are tubulated to be filled with gas or fluids, which fluids may be static or circulating. There may be an adhesive or ties on the outside of the base to allow the base to be fixed to an object.

The housing 14 can be configured to generate a contained space 16 which is typically domed shape, however, other configurations are encompassed, including but not limited to rectangular, cube, cuboid, cylinder, cone, square based pyramid, tetrahedron (i.e., triangle based pyramid), triangular prism, petagaonol prism, hexagonal prism, pentagonal pyramid, hexagonal pyramid, octagonal prism, etc.

Turning now to some additional features or attributes of the invention, the housing or frame may support a light source that provides light of different wavelengths to the contained space, said light source being controlled by and functions through the reusable electronic module. The housing or frame may further support an ultraviolet (UV) or blue light source that is located so as to provide the contained space with germicidal functions. The light source may be located outside or inside of the contained space in a volume that is in fluid connection with the contained space.

Figure 5:
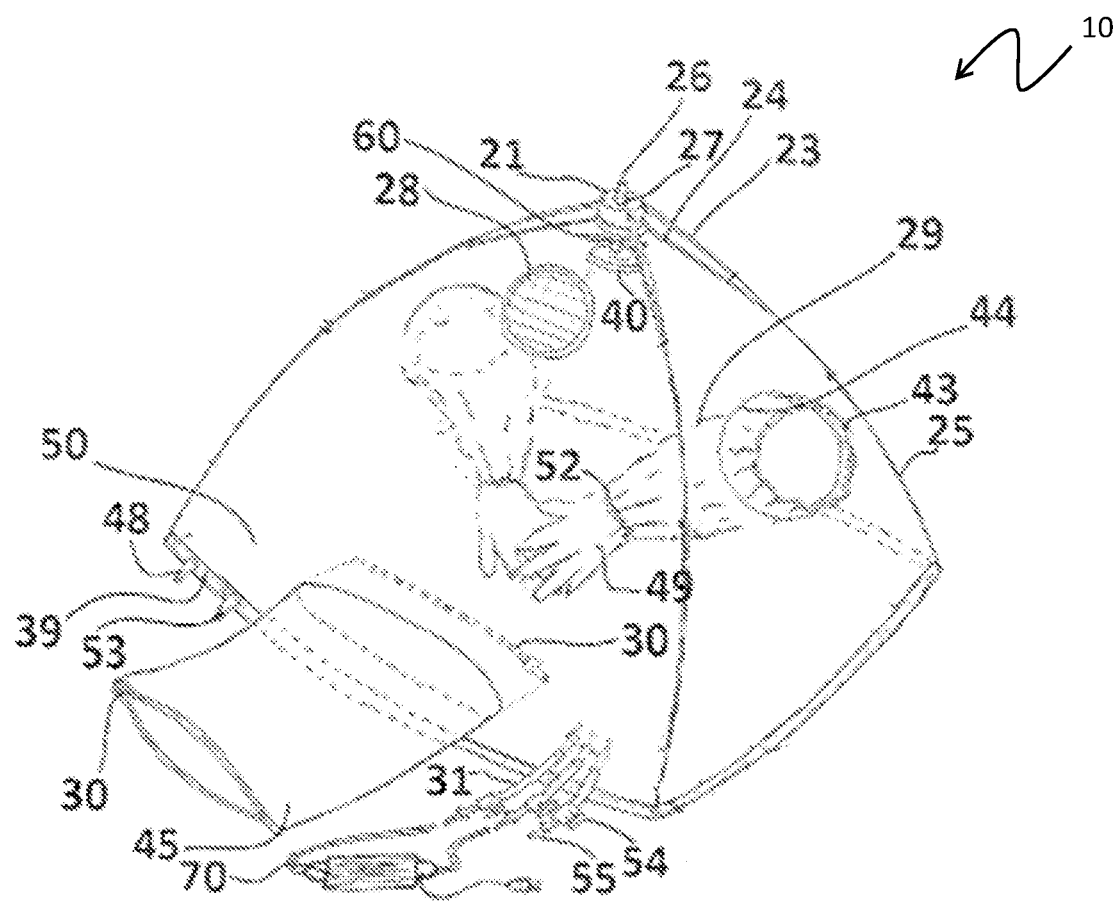
FIG. 5 is a detailed schematic of the neonatal incubator apparatus, showing different features of the disposable housing on the apparatus.

The housing may include one or more hand ports 29 or sleeves coupled to or supported by the housing membrane or canopy. The sleeves 29 may extend into the interior of the contained space and may be sized and shaped to accept the lower end of an arm of a person, as best seen in FIG. 5. The hand ports 29 or sleeves may comprise an elastic cuff 52 that fits tightly over the lower end of the arm. The housing may also include an air-lock sleeve 45 coupled to or supported by the membrane/canopy. The air-lock sleeve 45 may include mechanisms 30 at each end that allow the sleeve to be selectively opened and closed at both ends of the sleeve (one end external and the other internal to the contained space).

In some embodiments, the closed contained space 16 comprises one or more ports, e.g., inlet and outlet ports 31, 48, 53 that are in air communication with a control system module 17, for controlling the microenvironment of the disposable neonatal infant incubator apparatus 10. In some embodiments, an inlet or outlet port 31 connects the interior contained space 16 with the external environment, and can comprise a tube connected to, or through the housing sidewall 31, or into the base 48, 53. Each ports can optionally comprise a valve 54 and a tube coupling mechanism 55 at the external end, to allow attachment of tubes which connect to an inlet and/or outlet port in the housing of the control system module 17, thereby enabling air and/or fluid communication of the control system module 17 with the internal contained space 16 or base 50, thereby controlling the microenvironment of the contained space 16.

Accordingly, in some embodiments the system and apparatus disclosed herein encompasses a source of heating or cooling gases or air, or fluid to be passed through inlet and outlet port in the base 53 or the walls of the housing 31 when the neonatal infant apparatus is deployed to give thermal and structural support to an infant in the contained space. The housing 14 may have an outer layer that is impervious to fluids. The housing may further include one or more tubes that pass through the housing 31, 48, 53. The tubes, 31, 48, 53 may be for delivery of heat, humidity, gas, liquid, or mist into the interior contained space 16 to maintain the microenvironment or into a base 50 of the housing.

II. Control System Module

Incubators typically include one or more devices for regulating and sensing the temperature, flow, oxygen content, and relative humidity of the air in the incubator and for sensing the temperature of an infant in an effort to properly regulate the temperature and health of the infant within the incubator.

One aspect of the technology described herein relates to systems, methods and apparatus to control and maintain the microenvironment of the contained space 16 of the neonatal incubator apparatus 10 described herein. It will be appreciated that while control system module 17 has been described with regard to a specific embodiment, the control system module 17 may be provided in a variety of styles and designs in keeping with the teachings of this disclosure. The control system module 17 may also include other modules such as oxygen cells, scales, humidity sensors, and skin probes for sensing circulation, skin perfusion, heart rate, and respiration rate of the infant In some embodiments, a control system module 17 comprises a housing 18 for housing any one or more of: a power supply comprising a battery 32 or a voltage converter 33, or solar power (not shown), a microprocessor connected to the power supply, the microprocessor 34 comprising software for executing a program for controlling one or more of the functions (i) maintaining temperature within a pre-determined temperature range, (ii) maintaining humidity within a pre-determined humidity range, (iii) maintaining light at within a pre-defined wavelength range, (iv) maintaining the gas composition within a pre-determined range, and (iv) sterilizing and/or maintaining sterility of the air in the contained space 16. The control system module can comprise an interface 37 with one or more switches 38 for controlling power to microprocessor, and/or for controlling any one or more functions (i) to (v), as well as one or more outlet ports and a tube coupling system configured for air communication with an inlet port 31, 48, 53 on a disposable neonatal infant incubator apparatus 10.

In some embodiments, a control system module 17 functions to control the microenvironment of the contained space, wherein the control system module 17 functions to regulate any one or more of the following conditions in the contained space 16; temperature, humidity, light, gas composition, and sterility, where the control system module is in air communication and/or fluid communication with the contained space 16 by means of one or more tubes which connect to the tube coupling system on one or more inlet ports 31, 48, 53 of the disposable housing.

In some embodiments, the control system module 17 is configured to introduce air selected from a group consisting of: heated air, cooled air, humidified air, filtered air, room temperature air, predetermined gas concentrated air, air, and any combination thereof, into the contained space 17. In some embodiments, the control system module 17 is in air and/or fluid communication with the contained space 16 by means of one or more tubes connected to the tube coupling system 55 on one or more outlet ports 31, 48, 53 of the disposable housing.

In some embodiments, the control system module 17 is configured to receive air from the contained space by means of a tube in air and/or fluid communication with the outlet port 31, 53 of the contained space, wherein the control system module is configured to comprise a feedback mechanism for microenvironment of the contained space, where the microenvironment is selected from a group consisting of: temperature, humidity, pressure, airborne particle content, gas concentration, and any combination thereof, and where the control system module 17 is configured to maintain the quality of the microenvironment of the contained space in a predetermined value or value range.

Figure 11:
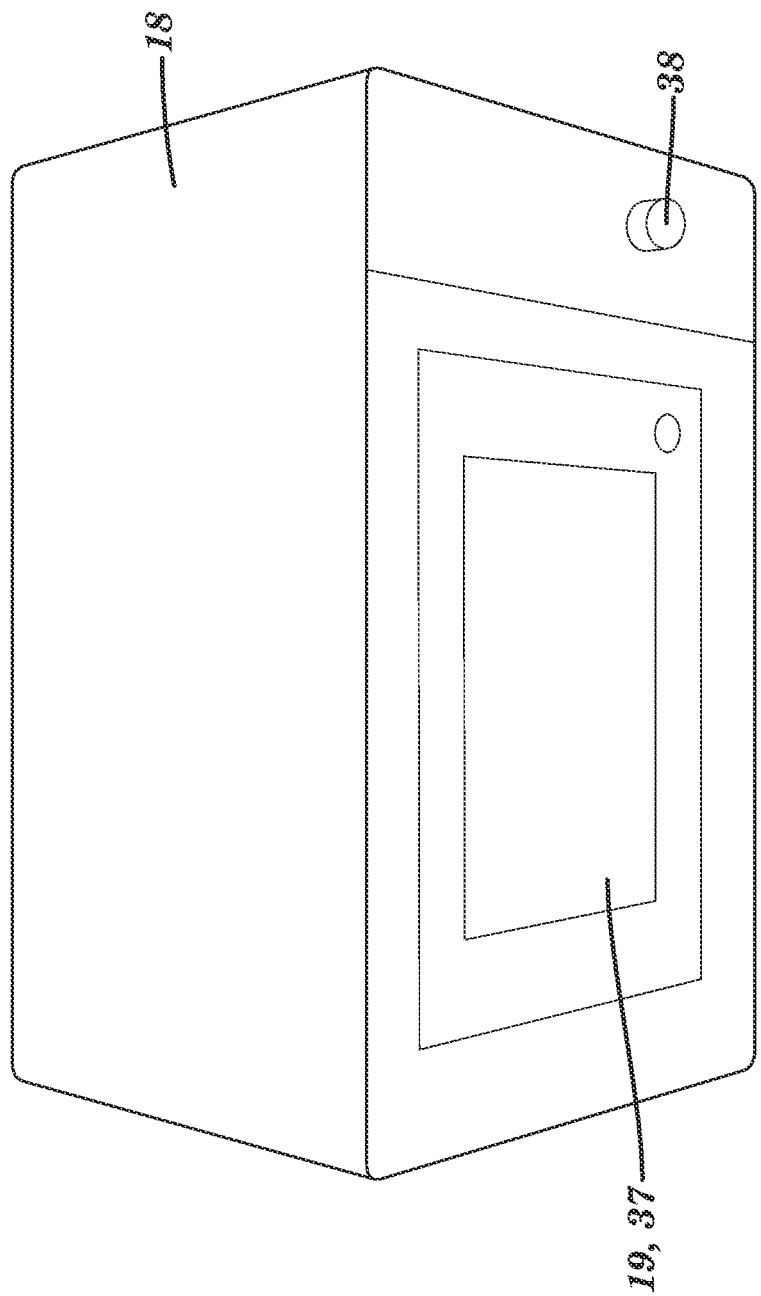
FIG. 11 shows an embodiment of the control system module housing, with interface and display.

Embodiments of the control system module are shown in FIG. 10 and FIG. 11. In some embodiments, the control system module 17 comprises a display 19 to display the status of the microenvironment of the contained space, and in some embodiments, the display is a touch screen display. In some embodiments, the interface 37 is touch screen interface and/or touchscreen display 19. In some embodiments, the control system module comprises a wireless communication module for controlling any one or more functions (i) to (v) from a remote device and/or location using a device that is wirelessly connected to the wireless communication module in the control system module.

In some embodiments, the control system module 17 comprises an air circulation system 72 mounted to the housing 18, the air circulating system 72 comprising an air filter 73, a heating element 74, and/or a cooling element 78, a blower motor 75 and a heat chamber 76, wherein the blower motor 75 blows air, prior to, or after the air has flowed through the air filter 73, into the heat chamber 76, and wherein the heat chamber 76 is connected to the outlet port on the housing. In some embodiments, an outlet of the housing comprises a tube coupling system, similar to 55, and is configured for air and/or fluid communication with an inlet port 31, 48, 53 on a neonatal infant incubator apparatus 10. In some embodiments, the air filter 73 is a HEPA filter, or other suitable air filter. In some embodiments, the air filter comprises an internal UV light source.

The control system module 17 comprises a battery 32, which is a 12V battery, and optionally is a replaceable and/or a rechargeable 12V battery. In some embodiments, the battery is recharged by solar power. The control system module 17 can comprise a solar power panel on the exterior of the housing 18 for recharging the battery 32. The control system module 17 can also comprise a voltage converter 33, which is a AC to DC voltage converter, and can convert 230V or 112V to 12V DC.

The control system module 17 can be used to control the microenvironment of the contained space in a neonatal incubator 10 because it is in fluid and/or air communication with the contained space. This because the closed contained space 16 comprises one or more ports, e.g., inlet and outlet ports 31, 48, 53 that are in air and/or fluid communication with a control system module 17, for controlling the microenvironment of a contained space 16 of a disposable neonatal infant incubator apparatus 10.

In some embodiments, the control system module comprises a sterilizer, for example, a UV or ozonizer, or other germicidal irradiation method, and can be used to exchange the air in the contained space with sterile air. In some embodiments, the control system module comprises a suction to suction air out of the contained space, such that air can be circulated from the contained space 16 past the sterilizer and back into the contained space 16. In some embodiments, a fan or blower motor 75 may be used to aid in circulation of the air.

In some embodiments, the control system module 17 comprises any module selected from a group consisting of at least one first venting module, at least one first heating/cooling module, at least one filter located adjacently to either the first venting module or the first heating/cooling module and any combination thereof. In some embodiments, the control system module 17 comprises at least one venting module configured to introduce air selected from a group consisting of: heated air, cooled air, humidified air, filtered air, room temperature air, predetermined gas concentrated air, air, air from an ozonizer, air mixed with gasses, e.g., from an oxygen canister or tank, and any combination thereof, into the contained space 16, and in some embodiments, the control system module 17 comprises a feedback mechanism for the air quality selected from a group consisting of: temperature, humidity, pressure, airborne particle content, gas concentration, and any combination thereof, configured to maintain the quality in a predetermined value or value range; and, in some embodiments, the control system module 17 comprises a fan, having at least one rotor rotating perpendicularly to a rotor's shaft, and further wherein the shaft is positioned in parallel to the outlet port of the control system module, to pump air, via the air communication system, into the contained space 16.

In some embodiments, the control system module 17 comprises at least one air inlet for collecting air stream from the outer environment; and/or can comprise at least one inlet for collecting air streamed from the contained space 16 of the neonatal infant apparatus 10; and/or at least one air outlet for introducing air towards the contained space 16 of the neonatal infant apparatus 10.

In some embodiments, the microprocessor 34 communicates through a display driver with display 19 permitting system status information to be displayed to a caregiver. A caregiver interfaces with microprocessor 34 through an interface 37, often a keypad and keypad interface 37, or a touchscreen keypad, to provide operation mode and set point information and also to request that specific system status information be displayed on display 19. A microprocessor 34 can provide additional indications of system status through any one or more of: LED interfaces, LEDs, audible alarms and/or speakers. Microprocessor 34 controls the oxygen solenoid of an oxygen container (not shown) through oxygen solenoid driver. Power to both the heater, air circulation system 72, and humidifier (not shown) are controlled by microprocessor 34 through AC power drivers. AC power drivers, fan driver and oxygen solenoid driver are coupled through analog interface with power supply, and any one or more of air flow sensor and ambient air temperature sensors. An alarm system is coupled through any one or more of: LEDs, a LED interface, speaker through audible alarm, oxygen solenoid of an oxygen container (not shown) through oxygen solenoid driver, blower motor, through fan driver and heater and humidifier through AC power drivers to provide appropriate control of those systems and indicators in the event of system failures. An alarm system can signal to fan driver in the event the system begins to operate outside of normal parameters.

As stated above, microprocessor 34 also monitors and controls the heater power (PH). A current transformer is in series with the power to heater and the humidifier. In some embodiments, the output of the current transformer is connected to an A/D converter 33 providing a means for controlling the incubator heater. Microprocessor 34 controls a solid state relay that controls the power to the heater 74 or cooling element 78.

Temperature, humidity, and oxygen concentration control is implemented by means of a forced air circulation system 72. A controlled amount of room air (illustratively approximately 7 liters per minute at 800 r.p.m.) is drawn through an air intake filter 73 by blower 75 (or impeller) located in the control system module housing 18. In addition to drawing fresh filtered air into the contained space 16 of the incubator, the blower 75 provides for the internal circulation of enclosed air in the contained space at a much greater flow than that of the fresh air inflow. In some embodiments, the total flow of fresh air and recirculated enclosure air is directed past one or more airflow sensors and around the heating elements of a heater 74. The air enters the contained space 16 of the infant incubator 10 through inlet slots 31, 48, 53. In some embodiments, the air can circulate past one or more sensor modules which contains air temperature sensors. After circulating within contained space 16, the air is then re-circulated down through outlet slot in the control system module housing 18 and back to blower 75. Temperature is regulated using either the air in the contained space 16, and/or or infant skin temperature as the controlling parameter; the desired mode (air temperature or skin mode) is illustratively selected by the caregiver through the interface (e.g., keypad and/or touchscreen).

In one embodiment, the air temperature of the contained space can be maintained from 68° F. (20° C.) to 99° F. (37° C.) or 99° F. (37° C.) to 102° F. (39° C.), as selected by a caregiver through up and/or down arrows, or other interface buttons or switches (e.g., a dial) of a keypad, touchscreen and/or the interface 37. The temperature selected from the above range is known as the air setpoint temperature and is stored in memory by microprocessor 34. The contained space 16 is monitored by one or more air temperature sensors located, for example, in an air intake of sensor module of the control sensor module 17 and compared by microprocessor 34 with the air setpoint temperature. Microprocessor 34 uses the air temperature information from the one or more air temperature sensors and the air setpoint temperature to generate a control signal supplied to the air circulation system 72 in AC power drivers which regulates the output of heater 74 or cooler 78 to bring the air temperature in the contained space 16 to, and maintain it approximately at, the air setpoint temperature. Those skilled in the art will recognize that the control signal for output of heater 74 or cooler 78 can be generated using known control algorithms based on the air temperature error, i.e. the difference between the measured temperature and the setpoint temperature. Among those known algorithms are proportional control, proportional integral (PI) control, proportional differential (PD) control and proportional integral differential (PID) control. Other known algorithms may be used to control the heater 74 and/or cooler 78.

The air temperature sensed by air temperature sensor is displayed on display 19. In some embodiments, the control system module can comprise a second sensor (not shown) within a sensor module, which serves as a backup to limit the maximum incubator temperature. In the event that the maximum air temperature in the contained space 16 is exceeded, heater 74 is shut off.

In some embodiments, the control system module 17 may also include other known sensors and switches, that provide input to regulate the operation of the blower motor 75 and to the heater controller to regulate heater operation. Examples of such sensors and switches include, but are not limited to, an oxygen sensor that would provide an indication to increase air flow when oxygen levels in the contained space 16 fall below a set level, an incubator warm-up mode indicator, ambient air temperature sensors, and similar sensors and switches.

In some embodiments, the microprocessor 34 of the control system module 17 is in communication with one or more skin temperature sensors on an infant for determining the temperature of the infant 62 located in the contained space 16, which compute if the air circulation system 72, should be activated, whether the temperature of the air in the contained space 16 should be increased or decreased. For illustration purposes only, a setpoint circuitry is implemented through an interface 37 of the control system module system 17, e.g., through a keypad, touchscreen or similar interface 37 and microprocessor 34. A caregiver using the interface 37 is able to enter a setpoint value ((BTSET) for infant skin temperature which is stored in memory by microprocessor 37. Illustratively, comparator is implemented in software or programming instructions driving microprocessor 37 which compares the current skin temperature data (BT) received through sensor module from sensor to the skin setpoint temperature ((BTSET) Illustratively, temperature differential circuitry and heater power differential circuitry are implemented in microprocessor 37 which runs a known algorithm for determining the time rate of change of the heater power and infant temperature using current values and stored values of infant temperature (BT) and heater power (PH).

In some embodiments, a skin temperature sensor provides an output indicative of the temperature of the infant 62. Sensor module and microprocessor 37 condition the output from skin temperature sensor to provide a current value of infant skin temperature (BT). In some embodiments a skin temperature sensor is a skin contacting probe of the type commonly available for use in attachment to a hospital patient. However, it is within the teaching of the disclosure to use one or more sensors capable of directly or remotely sensing the skin temperature of infant, including use of images, e.g., thermal images, and/or visual images from a camera detachably connected to the frame 12 and providing an output indicative of the skin temperature of the infant Other skin sensors can be used, for example, but not limited to, contact thermistors, digital thermometers, infra-red sensors, and the like.

Healthcare providers have found it advantageous to regularly circulate the air within an incubator enclosure so that proper oxygen content may be maintained within the enclosure. In one embodiment, even when the heating 74 or cooling element 78 of the air circulation system 72 are not being used, the blower motor 75 is operated at a sufficient speed to draw approximately seven liters of room air into contained space 16 to be mixed with the air in the contained space 16 replenish oxygen and remove carbon dioxide. The circulation of the air in the contained space by the air circulation system 72 is sufficient to so that proper oxygen content may be maintained within the contained space, however, body temperature of the infant must remain stable, given this air circulation. Therefore, in some embodiments, the blower motor 75 runs continuously when an infant 62 is in the contained space 16 to ensure proper air circulation to allow oxygen to be replenished and excess carbon dioxide to be removed. It is within the scope of the invention for oxygen replenishment and carbon dioxide removal to be accomplished with intermittent operation of the blower motor 75.

In some embodiments, an oxygen tank or canister is fluidly connected with the air circulation system 72 control system module such that oxygen levels in the contained space can be maintained at a certain pre-determined oxygen concentration. In some embodiments, the oxygen concentration in the contained space is higher than normal air, i.e., a saturated oxygen environment, in instances where the infant is need of apnea treatment, or treatment of hypoxia with passive treatment instead of the subject requiring a CPAP mask or other similar CPAP treatment.

III. Use of the Apparatus as a Neonatal Incubator

FIG. 3 illustrates one embodiment of the neonatal intensive care infant incubator ("NICI") apparatus 10, which comprises an external frame 12 in the open configuration, and the disposable housing 14, detachably connected to the interior of the external frame 12. The external frame 12 provides a support structure, i.e., acts an exoskeleton to the disposable housing 14. The disposable housing 14, has sidewalls and a base 50 and therefore when it is attached to the frame, it forms a closed containment space 16. When the disposable housing 14 is attached the frame 12 which is the expanded, open configuration, the containment space 16 is configured and provides sufficient space for the full body 62, or part 65 of a neonatal subject's body. The disposable housing 14, can form a contained space 16 that is typically dome shape, although other configurations are encompassed as discussed herein. The 3D shape of the contained space 16 is dependent on the number of arms of the frame and/or the 2D shape of the base of the housing 14. The housing 14 which creates the closed contained space 16 can have one or more contained compartments 18, as illustrated in the embodiment shown in FIG. 3.

The neonatal infant incubator apparatus and control system module as disclosed herein can be used to conduct a wide array of procedures, surgeries or operations on an infant in the contained space, by placing the operator's hand into the hand ports 29 to get access to the infant. In some embodiments, as the hand ports can comprise gloved portions, an operator's hands are isolated from, and do not directly contact, items within the contained and controlled space. Because the control system module operates under low voltage, and comprises a 12V battery, the neonatal infant incubator apparatus and control system module can be used in situations where no conventional medical establishment is available, such as in ambulatory and emergency services, third world countries, in areas of conflicts, rural areas, or in a regular clinical setting. This neonatal infant incubator apparatus and control system module is also useful for treatment and incubating infants in evacuation areas, and where normal neonatal infant care is not accessible or available. The neonatal infant incubator apparatus and control system module allows the introduction of various substances and/or control of the contained environment. The neonatal infant incubator apparatus and control system module allows for infant and neonatal care on site with a high degree of care to the infant, with respect to maintaining temperature, oxygen, humidity and gas composition in the microenvironment of the incubator. The neonatal infant incubator apparatus and control system module can be operated by persons with low level of skill and an operator can reach and treat the infant through the hand-ports, or gloved sleeves without direct contact with the infant, if necessary. The control system module can comprise sterilizers, and air circulation systems thus enabling control of the temperature and gas composition of the neonatal infant incubator apparatus. Positive air pressure can be maintained through a pressurized air-canister connected to, and controlled by the control system module, which can control flow into the incubator apparatus via air- and fluid communication access tubes. In some instances, the control system module can comprise a vacuum device, thereby controlling a negative pressure in the contained space of the incubator, therefore enabling containment of any viruses, bacteria or biohazardous waste to be contained in the contained space of the incubator.

The neonatal infant incubator apparatus and control module system provides a sterilized/aseptic incubator space for an infant, where the incubator housing is disposed of after use. Typically, the housing of a neonatal infant incubator is used for 1-7 days, or between 7-10 days, after which the housing is detached from the frame and disposed of, and a new housing is detachably connected to a frame and air- and fluid connected to the control module system. In general, the agents are delivered through the sealable air-locked sleeves. To deliver any object inside the neonatal infant incubator apparatus, unseal and open the outside portion of the sleeve 45, deliver the object to the inside of the sleeve 45, reseal the outside sleeve portion 30, then from inside the apparatus and by using the gloved sleeves unseal and open the inner sleeve portion 30 and bring the object into the inner contained space. Positive air pressure from the control system module, e.g., from the air circulation system 72 can be maintained at all times to prevent contamination, in addition to the use of a sterilizer if desired.

The neonatal infant incubator apparatus and control system module can be used in the field of preterm born infants as an incubator and/or treatment station. One sleeve can be made large enough to deliver large objects, with air-lock capability, and is referred to as a patient access door or port 36. This contained and sealed system will provide the operator and the surrounding environment complete protection and vice versa, and safe disposal of biological, medical, and/or other potentially hazardous materials with significantly lower cost than current methods, while being operated with low voltage (including a 12V battery), and therefore is a portable system for use at remote locations and/or where power supply is limited or inaccessible.

The neonatal infant incubator apparatus and control system module can be used when and wherever a neonate is in need of care, where there is insufficient infrastructure for incubating a neonate, or where skilled infant caretakers are limited, or lack of availability of the appropriate physical incubators for babies. The neonatal infant incubator apparatus and control system module disclosed herein is flexible and versatile, and is small, lightweight, cost effective, and provides incubator care for infants in situations which would not otherwise have such care, therefore dramatically saving lives.

IV. Kits

Other aspects of the technology relate to kits comprising the housing 14 and a frame 12, which can be assembled by the user into the neonatal infant incubator apparatus 10. In some embodiments, the kit comprises the control system module 17.

It is to be understood that the above-referenced description is illustrative of the invention. Numerous modifications and alternative arrangements can be devised without departing from the spirit and scope of the present invention. While the invention has been shown in the drawings and described above in connection with the exemplary embodiment (s) of the invention, it will be apparent to those of ordinary skill in the art that numerous modifications can be made without departing from the principles and concepts of the invention.

The invention claimed is:

1. A controlled environment neonatal infant incubator system comprising:
   a. a neonatal infant incubator apparatus including:
      i. a frame,
      ii. a disposable housing detachably connected to the frame, the disposable housing comprising a plurality of sidewalls, a base, and at least one inlet port with a valve and a tube coupling system, and at least one air-locked infant access door in at least one sidewall, wherein the frame is a collapsible frame, and includes a collapsed configuration or expanded configuration, and wherein the disposable housing forms an air-tight contained space configured for an infant when detachably connected to the frame in the expanded configuration;
   b. a control system module configured to control the microenvironment of the contained space, the control system module regulating temperature and gas composition in the contained space, the control system module including at least one tube that is in air communication with the contained space via the at least one inlet port of the disposable housing.

2. The system of claim 1, wherein the control system module further regulates at least one of humidity, light and sterility in the contained space.

3. The system of claim 1, wherein the housing further comprises at least one hand port in at least one sidewall.

4. The system of claim 1, wherein the housing further comprises at least one air-locked sleeve in at least one side wall.

5. The system of claim 1, wherein the housing further comprises at least one outlet port in at least one sidewall, the outlet port having a valve and a tube coupling system.

6. The system of claim 5, wherein the control system module includes at least one tube that is in air communication with the contained space via the at least one outlet port of the disposable housing.

7. The system of claim 1, wherein at least one sidewall of the housing includes a plurality of layers.

8. The system of claim 1, wherein the base of the housing includes a plurality of layers.

9. The system of claim 7, wherein the at least one sidewall, or the base, or both, are inflatable.

10. The system of claim 1, further comprising a HEPA filter or other air-filtration laminar flow system in at least one of the plurality of sidewalls.

11. The system of claim 1, further comprising a fan in the contained space, the fan being attached to the frame.

12. The system of claim 1, further comprising a light source that provides light to the interior of the contained space, the light being detachably connected to the frame.

13. The system of claim 12, wherein the light source is an ultraviolet (UV) light source or infrared (IR) light source.

14. The system of claim 1, further comprising a camera detachably connected to the frame, the camera monitoring at least one of visible or non-visible spectrum.

15. The system of claim 14, wherein the camera is operatively connected to the controller system module.

16. The system of claim 1, the system control system module being operatively connected to at least one sensor in the contained space, the sensor configured to monitor any one of: temperature, humidity or gas composition of the air in the contained space.

17. The system of claim 1, wherein the control system module for controlling the microenvironment of the contained space comprises a housing for containing any one or more of:
   a. a power supply comprising a battery or a voltage converter, or both,
   b. a microprocessor connected to the power supply, the microprocessor comprising software for executing a program for controlling one or more of the functions:
      i. maintaining temperature within a pre-determined temperature range,
      ii. maintaining humidity within a pre-determined humidity range,
      iii. maintaining light at within a pre-defined wavelength range,
      iv. maintaining the gas composition within a pre-determined range, and
      v. maintaining sterility of the air in the contained space,
   c. an interface with one or more switches for controlling power to microprocessor, and for controlling any one or more functions (i) to (v);
   d. an outlet port and a tube coupling system configured for air communication with an inlet port on a disposable neonatal infant incubator apparatus.

18. The system of claim 17, wherein the battery is a 12V battery.

19. The system of claim 1, wherein the disposable housing forms an air and liquid impermeable contained space.

20. The system of claim 1, wherein the plurality of sidewalls are transparent.

* * * * *